United States Patent
Roffler et al.

(10) Patent No.: US 11,013,690 B2
(45) Date of Patent: May 25, 2021

(54) ESTERIFICATION/SAPONIFICATION-BASED METHOD FOR LIPOSOMAL ENCAPSULATION OF HYDROPHILIC GLUCURONIDES

(71) Applicant: Academia Sinica, Taipei (TW)

(72) Inventors: Steve R. Roffler, Taipei (TW); Pierre-Alain Burnouf, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/067,643

(22) PCT Filed: Jan. 4, 2017

(86) PCT No.: PCT/US2017/012129
§ 371 (c)(1),
(2) Date: Jul. 2, 2018

(87) PCT Pub. No.: WO2017/120190
PCT Pub. Date: Jul. 13, 2017

(65) Prior Publication Data
US 2019/0008771 A1    Jan. 10, 2019

Related U.S. Application Data

(60) Provisional application No. 62/274,519, filed on Jan. 4, 2016.

(51) Int. Cl.
*A61K 9/127*        (2006.01)
*A61K 47/54*        (2017.01)
(Continued)

(52) U.S. Cl.
CPC ............ *A61K 9/1278* (2013.01); *A61K 9/127* (2013.01); *A61K 47/542* (2017.08);
(Continued)

(58) Field of Classification Search
CPC .... A61K 9/127; A61K 9/1278; A61K 47/542; A61K 47/549; A61K 47/6911; A61P 35/00
See application file for complete search history.

(56) References Cited

U.S. PATENT DOCUMENTS 5,169,636 A    12/1992  Nanba et al.
5,443,839 A *   8/1995  Meybeck ................. A61K 8/14
                                                424/401
(Continued)

FOREIGN PATENT DOCUMENTS

CN        1320605 A       11/2001
WO     WO-9833484 A1       8/1998

OTHER PUBLICATIONS

Zzzztrosko, J.E., et al in Mutation Research 480-481, pp. 219-229, 2001.*
(Continued)

*Primary Examiner* — Gollamudi S Kishore
(74) *Attorney, Agent, or Firm* — Faegre Drinker Biddle & Reath LLP

(57) ABSTRACT

Described herein is a method for loading a hydrophilic compound into liposomes after addition of an alkylester group to form an esterified compound. After loading, the alkylester is hydrolyzed to reform the hydrophilic compound inside the liposomes. Also described is a method for loading drugs under a glucuronide methylester form into liposomes. The glucuronide methylester form of the drug is saponified to a glucuronide form of the drug inside the liposomes for better drug retention. The glucuronide residue conjugated to drugs can be removed inside cells to regenerate the parental drug upon cell uptake, liposomal degradation and enzyme hydrolysis. In case of cancer, this method can be used to safely deliver drugs to tumors.

24 Claims, 45 Drawing Sheets

(51) Int. Cl.
*A61K 47/69* (2017.01)
*A61P 35/00* (2006.01)
(52) U.S. Cl.
CPC ........ *A61K 47/549* (2017.08); *A61K 47/6911* (2017.08); *A61P 35/00* (2018.01)

(56) References Cited

U.S. PATENT DOCUMENTS

| | | | |
|---|---|---|---|
| 5,877,158 A | 3/1999 | Bosslet et al. | |
| 2008/0045575 A1* | 2/2008 | Van Dyke | A61K 9/0063 514/369 |
| 2008/0171078 A1* | 7/2008 | Gray | A61K 9/127 424/450 |
| 2009/0227617 A1 | 9/2009 | Aben et al. | |
| 2012/0288558 A1* | 11/2012 | Gabizon | A61K 9/1271 424/450 |
| 2013/0177629 A1 | 7/2013 | Martin et al. | |
| 2014/0031535 A1 | 1/2014 | Jeffrey | |
| 2015/0290184 A1* | 10/2015 | Monte | A61K 9/1272 424/450 |

OTHER PUBLICATIONS

Angenault,s,m et al in Bioinorganic & Medicinal Chemistry Letters, vol. 13, pp. 947-950 (2003).*
International Search Report for PCT/US2017/012129 dated Mar. 23, 2017.
Written Opinion of the International Searching Authority for PCT/US2017/012129 dated Mar. 23, 2017.
Graaf et al., "A methylester of the glucuronide prodrug DOX-GA3 for improvement of tumor-selective chemotherapy", Biochemical Pharmaco., vol. 68, No. 11, Dec. 1, 2004, pp. 2273-2281.

* cited by examiner

ESTERIFICATION/SAPONIFICATION-BASED METHOD FOR LIPOSOMAL ENCAPSULATION OF HYDROPHILIC GLUCURONIDES

CROSS-REFERENCE TO RELATED APPLICATIONS

This application is a national stage application (under 35 U.S.C. § 371) of PCT/US2017/012129, filed Jan. 4, 2017, which claims benefit of U.S. Application No. 62/274,519, filed Jan. 4, 2016, both of which are incorporated herein by reference in their entirety.

TECHNICAL FIELD

The present disclosure is related to the loading of glucuronide esters, for example glucuronide methylesters, and internal saponification to glucuronides in pH gradient liposomes.

BACKGROUND

Liposomes are biologically stable lipid vesicles engineered to carry drugs to targeted tissues, and several liposomal drugs are now in clinical use. The majority of nanoparticles approved by the FDA or in clinical phase II/III trials for the delivery of anticancer drugs are liposomes[1-3]. They present numerous advantages such as being biocompatible[4], non-immunogenic[5], stable in the circulation but able to release 100% of their payload upon degradation at targeted sites. Major drawbacks of liposomal encapsulation include difficulty in actively loading drugs into the liposomes and poor retention of hydrophobic drugs in the liposomes[6-8]. Premature "burst" release and continuous leakage of drugs from liposomes not only produces adverse side effects to healthy tissues but also diminishes the therapeutic efficacy by reducing the targeted payload. Hydrophobic drugs can also destabilize the liposomal membrane, causing even faster release of encapsulated drugs[9]. It was also observed that loading of hydrophobic drugs is limited by rapid formation of needle-like precipitates within the membranes[10]. On the other hand, hydrophilic drugs loaded in liposomes accumulate in the aqueous core and do not interact with the liposome membrane. These formulations are more stable and less susceptible to the issues described above. Poor solubility in the liposome membrane, however, make active loading of high concentrations of hydrophilic drugs into liposomes difficult.

The drug's hydrophobicity can be reduced by addition of hydrophilic group, such as a sugar moiety. A good example of dramatically enhanced hydrophilicity after sugar conjugation is the addition of a glucuronide residue on the parental structure of a hydrophobic drug[11-15]. Attachment of a glucuronide moiety to a hydrophobic drug is expected to greatly reduce leakage of the drug from liposomes. This, in turn, may facilitate stable retention in liposomes of hydrophobic drugs, thereby reducing drug leakage for less systemic toxicity as well as allowing more drug to reach target tissues. However, effective methods have not been disclosed for the loading of glucuronide drugs into liposomes.

Drug loading methods can be divided in two categories: passive and active. Passive methods rely on entrapment of drug within liposomes during the formation of vesicles from a dry lipid film. In passive methods, the concentration inside the liposomes equals the concentration outside in the bulk media. Active methods rely on a chemical driving force resulting in accumulation of compounds inside preformed liposomes. The loading efficiency provided by active methods can be significantly greater than those attained by passive loading.

A method for loading of amphiphilic weak acids in liposomes was developed by Barenholz et al. (U.S. Pat. No. 5,939,096[16]) and Clerc et al. relying on a calcium acetate-based transmembrane gradient[17]. In this method, the weak acid is readily membrane permeable at low pH and therefore penetrates into liposomes. It then gets trapped inside after ionization at internal high pH. Internal acetate is used as a proton shuttle from inside to outside of the liposome, which aims to sustain an internal high pH while weak acids are loaded. In contrast, the low membrane permeability of calcium ions produces a high internal calcium concentration, which precipitates the weak acid drug inside the liposome for better stability. The method however was developed for amphiphilic weak acids and is not suited for hydrophilic weak acids such as glucuronides. Glucuronides, which are members of weak acid family, are characterized by a very poor affinity to lipid membranes and are strongly in favor of the aqueous phase, meaning they are excluded from the range of amphiphilic compounds.

A method is described here to efficiently load glucuronide derivatives of drugs based on the loading of alkylester, for example methylester glucuronide derivatives of drugs. The conditions are set to allow conversion of the methylester glucuronide derivative to a hydrophilic glucuronide derivative inside the liposomes. In addition, the parental drug is regenerated after uptake of liposomes into target cells and enzymatic cleavage of the glucuronide group from the drugs. Numerous glucuronides of anticancer drugs that have been synthesized[11-14, 18-44] (Supplementary Table 1), but no methods have been proposed to actively load them into liposomes.

SUMMARY

Covalent addition of a glycosidic residue (such as a glucuronide residue by glucuronidation) is a way to create more water soluble derivatives of anticancer drugs[11-15]. A "glucuronide" in this context can be any substance produced by linking glucuronic acid to another substance via a glycosidic bond or a chemical linker. To date, numerous glucuronides of anti-cancer drugs have been synthesized and many other types of glucuronides are commercially available[11-14, 22, 23, 27, 28, 38, 41, 43, 45-49]. Following chemical modification, these drugs become much more water soluble. Knowing these characteristics, loading of glucuronides could provide better liposomal retention of hydrophobic drugs. In addition, injection of free glucuronides of anticancer drug is also affected by rapid clearance[50]. Liposomal encapsulation can help prolong the half-life of glucuronides in-vivo.

In one aspect is provided the description of the loading of glucuronides in liposomes having an internal pH that is greater than the external pH. The internal pH may be greater than 7 and the external pH may be less than 7. The internal pH can be about 8 and the external pH can be about 5. Demonstrated herein is the loading of glucuronide derivatives of 2 hydrophobic anticancer compounds, 9-aminocamptothecin (9AC), 5,6-dihydro-4H-benzo[de]quinoline-camptothecin (BQC) and 1 hydrophobic fluorescent compound 4-methylumbelliferone, which was recently found to be a promising non toxic therapeutic agent against the development of prostate cancer[51].

The loading of glucuronides is achieved under an alkylester, particularly a methylester, form (glucuronide-mE), which is a more membrane permeable form of glucuronide. The glucuronide-mE is added to the external medium of liposomes where the pH (external pH) value is less than the pH of the medium in the core of the liposomes (internal pH). After loading of glucuronide-mE, the internal pH is sufficient to spontaneously hydrolyze the methylester group and reform the glucuronide by saponification inside the liposome.

In another aspect, the comparison between the liposomal retention of hydrophobic drugs before and after glucuronidation was achieved. Non-glucuronide and glucuronide forms of the compounds are loaded into liposomes and drug stability is monitored in biological environment.

In another aspect, the killing of cancer cells in-vitro or the reduction of the size of a tumor in a mammal is described. Any of the liposomes loaded with glucuronide described herein are administered to the mammal in an amount effective to reduce the size of the tumor and with minimal toxicity to the mammal.

In another aspect, the comparison of the pharmacokinetics of free glucuronide drug to glucuronide drug encapsulated in liposomes was evaluated. Free glucuronide and liposomal glucuronides were injected intravenously and blood clearance was monitored.

In another aspect, the regeneration of the hydrophobic drug after cellular uptake of glucuronides loaded liposomes and lysosomal enzyme beta-glucuronidase cleavage was demonstrated in in-vitro cancer cell culture and mammal bearing human tumors.

In another aspect, it is demonstrated that the amount of regenerated drug (active form) is significantly higher in tumors than in the blood circulation.

In another aspect a method is described wherein a glucuronide form of a parental hydrophobic drug is prepared. This hydrophilic form of the drug is then esterified by conjugating an alkylester group to the hydrophilic form of the drug (for example a methylester), thus forming an esterified compound. This esterified compound is added to a liposome suspension by the methods described in more detail herein. After administration of the liposomes to cancer cells, it is observed that the liposomes are degraded in lysosomes in the cells, releasing the glucuronidated form of the drug into the lysosomes. Beta-glucuronidase (an enzyme) in the lysosomes can then cleave the glycosidic bond between the glucuronide and drug or spacer-drug, thereby regenerating the parental compound.

Additional aspects and advantages will appear from the drawings and the detailed description.

BRIEF DESCRIPTION OF THE DRAWINGS

Embodiments are illustrated by way of the accompanying drawings, in which.

within the cells is observed. (red is liposomes, magenta is lysosomes, and green is fluorescein)

Figure 35:
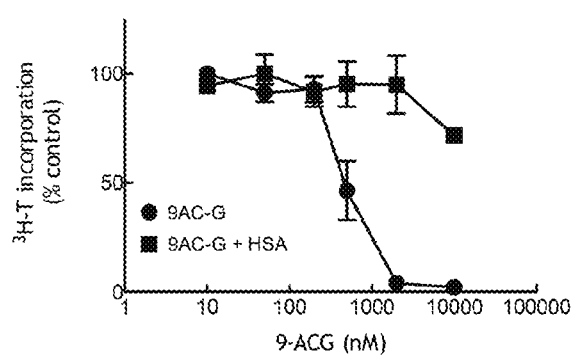

FIG. 35 illustrates the neutralizing effect of human serum albumin on free 9AC-G. Human hepatocellular carcinoma cells (HCC36) were exposed to free 9AC-G with or without human serum albumin (40 mg/mL) for 24 hours. Cell proliferation was observed by $^3$H-thymidine incorporation assay. Human serum albumin inhibits the potency of free 9AC-G that is not loaded into liposomes. n=3, Error bars, SD.

Figure 36:
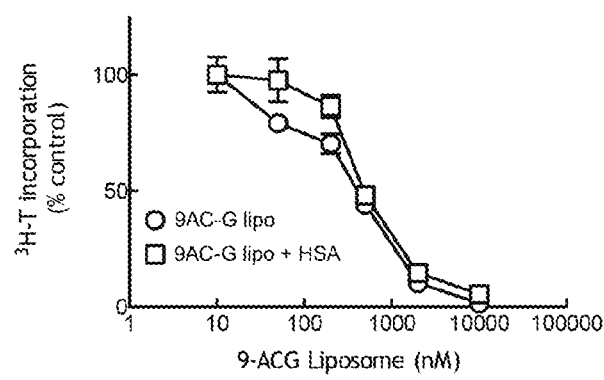

FIG. 36 illustrates the inability of human serum albumin to neutralize 9AC-G after liposomal loading. Human hepatocellular carcinoma cells (HCC36) were exposed to liposomal 9AC-G with or without human serum albumin (40 mg/mL) for 24 hours. Cell proliferation was observed by $^3$H-thymidine incorporation assay. Human serum albumin outside of liposomes does not inhibit the potency of 9AC-G that is loaded into liposomes. n=3, Error bars, SD.

Figure 37:
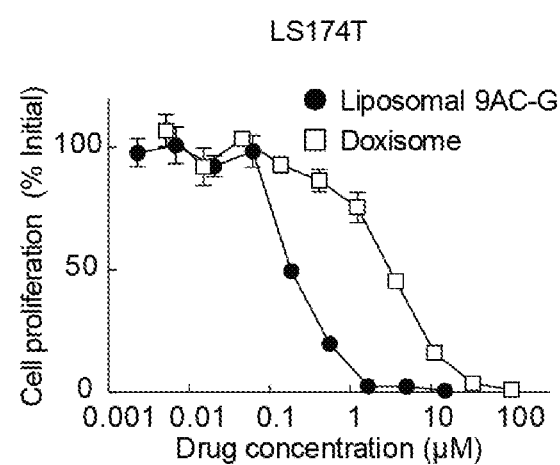

FIG. 37 illustrates the growth inhibition of 9AC-G liposomes compared to doxorubicin liposomes (Doxisome®) against LS174T human colon cancer cells in a $^3$H-thymidine incorporation assay. Cells were seeded at 5000 cells/well in 96 well plates and incubated overnight. Graded concentrations of liposomal drugs were added to the cells for 24 hours and thymidine incorporation was measured. n=3, Error bars, SD.

Figure 38:
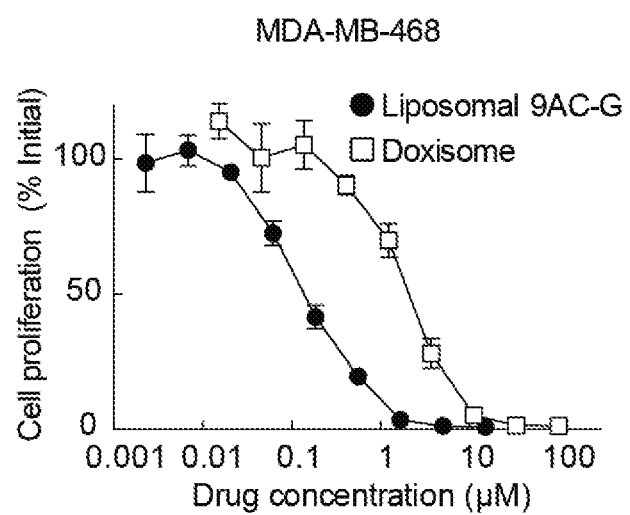

FIG. 38 illustrates the growth inhibition of 9AC-G liposomes compared to doxorubicin liposomes (Doxisome®) against MDA-MB-468 human breast cancer cells in a $^3$H-thymidine incorporation assay. Cells were seeded at 5000 cells/well in 96 well plates and incubated overnight. Graded concentrations of liposomal drugs were added to the cells for 24 hours and thymidine incorporation was measured. n=3, Error bars, SD.

Figure 39:
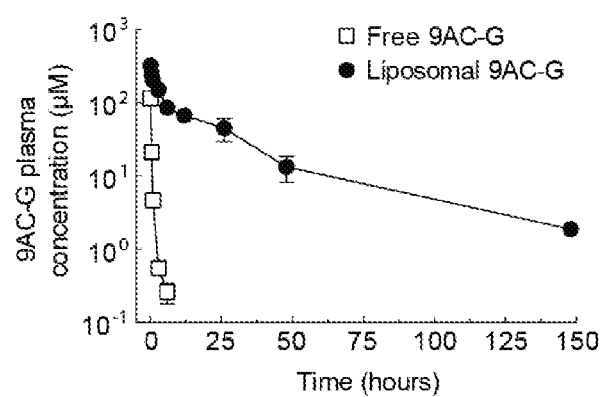

FIG. 39 illustrates the pharmacokinetics in mice of free 9AC-G compared to liposomal 9AC-G. A dose of 25 mg/kg of either free 9AC-G or liposomal 9AC-G was injected intravenously by the tail of NOD/SCID mice. Blood samples were collected at different times and the concentration of 9AC-G was determined by HPLC. n=3, Error bars, SD.

Figure 40:
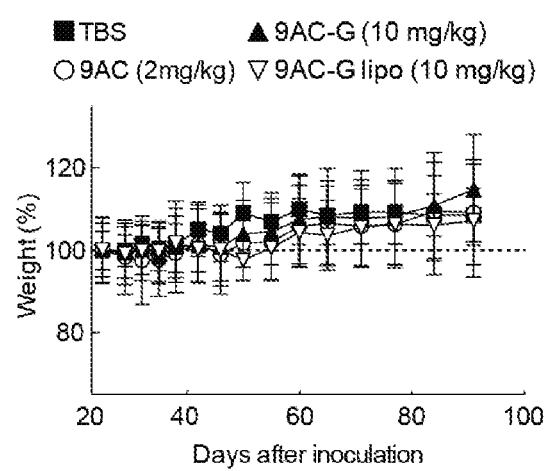

FIG. 40 illustrates the in-vivo toxicity of free 9AC, 9AC-G, and liposomal 9AC-G. NOD/SCID mice were inoculated subcutaneously with $10^7$ MDA-MB-468 cells. When tumors reached 75 to 100 mm$^3$ the treatment started at one injection per week for a total of 4 treatments. The toxicity was monitored by body weight loss. n=7, Error bars, SD.

Figure 41:
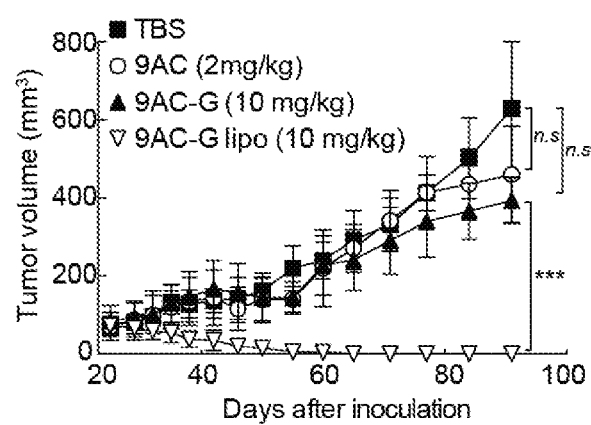

FIG. 41 illustrates the in-vivo anti-tumor activity of liposomal 9AC-G. NOD/SCID mice were inoculated subcutaneously with $10^7$ MDA-MB-468 cells. When tumors reached 75 to 100 mm$^3$ the treatment started at one injection per week for a total of 4 treatments. Figure represents the tumor volume evolution. n=7, Error bars: SD. Differences in tumor sizes between groups were examined for statistical significance using one-way ANOVA followed by Dunnettt's multiple comparisons. Stars indicate significance; n.s=non-significant and p<0.0001 (***)

Figure 42:
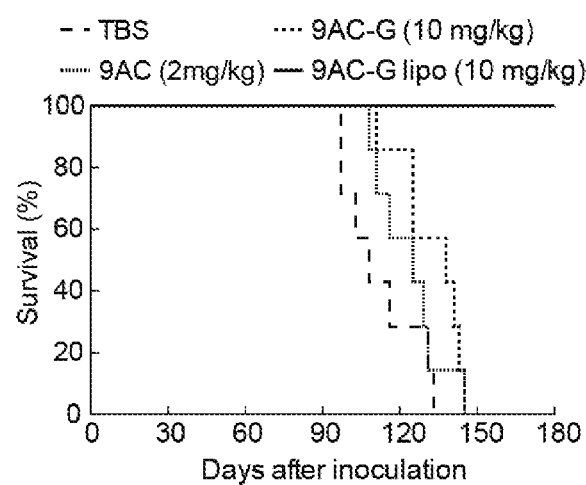
Figure 43:
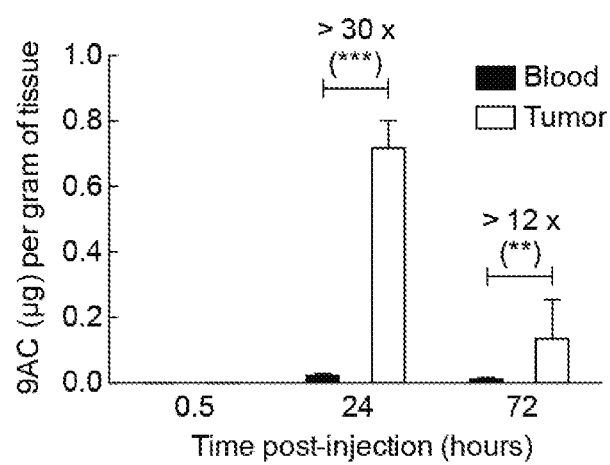

FIG. 42 illustrates the mice survival after treatment with 9AC, 9AC-G or 9AC-G liposomes. n=7, Error bars, SD FIG. 43 illustrates the accumulation of parental drug 9AC in tumors compared to blood of mice bearing MDA-MB468 tumors after intravenous injection of 9AC-G liposomes. n=3, Error bars, SD. Two-tailed unpaired Student's T-test was used for statistical analysis. Stars indicate significance; p<0.001 () and p<0.0001 (*).

Figure 44:
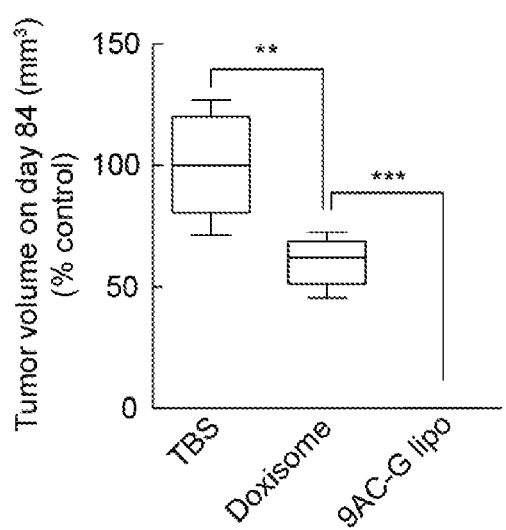

FIG. 44 illustrates the tumor growth of MDA-MB-468 human breast cancer cells ($10^7$ cells in 100 µL PBS) injected subcutaneously in twelve to sixteen-week old female NOD/SCID immunodeficient mice. When tumors reached sizes from 75 mm$^3$ to 100 mm$^3$, groups of 7 mice were treated at weekly intervals for four times with intravenous injections of 9AC-G (10 mg/kg) or doxorubicin liposomes (Doxisome®, 1 mg/kg). n=7, Error bars, SD. Differences in tumor sizes between groups were examined for statistical significance using one-way ANOVA followed by Dunnettt's multiple comparisons. Stars indicate significance; p<0.001 () and p<0.0001 (*)

Figure 45:
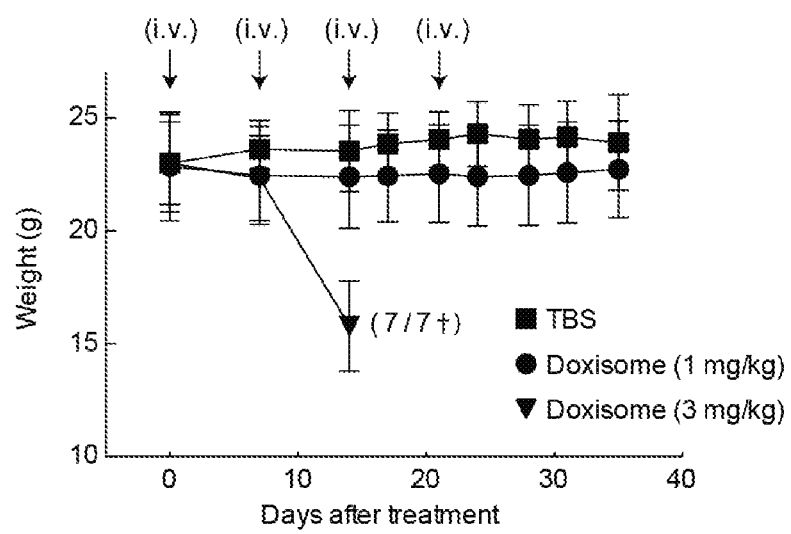

FIG. 45 describes the toxicity of doxorubicin liposomes in groups of 7 mice treated 4 times weekly with intravenous injections of doxorubicin liposomes (Doxisome®) at either 1 mg/kg or 3 mg/kg. The toxicity was assessed by body weight loss. n=7, Error bars, SD.

Table 1 shows the 50% growth inhibitory concentration (IC$_{50}$) of 9AC-G liposomes and doxorubicin liposomes. Assays were performed on 3 human colon cancer cell lines (LS174T, HT29, and HCT116), 3 human lung cancer cell lines (CL1-5, NCI-H2170, and SK-MES-1) and 1 human breast cancer cell line (MDA-MB-468). Average fold improvements of 9AC-G liposomes as compared to doxorubicin liposomes are displayed as well as the statistical significance of difference in mean IC$_{50}$ values calculated by a two-tailed unpaired Student's T-test.

Supplementary Table 1 describes a non-exhaustive list of already synthesized glucuronides of anticancer drugs. In some cases, references include glucuronides characterization and biological activity.

DETAILED DESCRIPTION

While the appended claims set forth the features of the present techniques with particularity, these techniques, together with their objects and advantages, may be best understood from the following detailed description taken in conjunction with the accompanying drawings.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

In one aspect is provided a method for loading an esterified compound (glucuronide-mE) into liposomes. A liposome suspension can be prepared with an external pH lower than 7 and an internal pH sufficiently high to convert the esterified compound to an hydrophilic compound. The esterified compound can be prepared by conjugating an alkylester group to the hydrophilic compound. The alkylester group may be a methylester group. The esterified compound can be added to the liposome suspension, where the esterified compound is loaded into the liposomes. In the liposomes, the esterified compound may be saponified to generate the hydrophilic compound (glucuronide). The method can be effective to increase the liposomal retention of a hydrophobic compound in a glucuronidated hydrophilic form. The method can be effective to load a glucuronidated hydrophilic form of the hydrophobic compound into the aqueous core of a liposome. The method can also be effective to load the glucuronide into the aqueous core of a liposome and improve the in-vivo half-life of the hydrophilic compound. The internal pH can be greater than 7 and the external pH can be less than 7. Alternatively, the internal pH can be from 7.5 to 8.5 and the external pH can be from 4.5 to 5.5. Alternatively, the internal pH is about 8 and the external pH is about 5. Alternatively, the internal pH is 8 and the external pH is 5.

In another aspect is provided a method for loading a glucuronide-mE into liposomes. A liposome suspension can be prepared with an external pH lower than 7 and an internal pH sufficiently high to convert the glucuronide-mE to a glucuronide. The glucuronide-mE can be prepared by conjugating a methylester group to the glucuronide. The glucuronide-mE can be added to the liposome suspension, where the glucuronide-mE is loaded into the liposomes. In the liposomes, the glucuronide-mE may be saponified to generate a glucuronide. The method may be effective to increase the liposomal loading and retention of the glucuronide. The method may be effective to improve the in-vivo half life of the glucuronide. The internal pH can be greater than 7 and the external pH can be less than 7. Alternatively, the internal pH can be from 7.5 to 8.5 and the external pH can be from 4.5 to 5.5. Alternatively, the internal pH is about 8 and the external pH is about 5. Alternatively, the internal pH is 8 and the external pH is 5.

In another aspect is provided a method of preparing a liposome loaded with a glucuronide. The glucuronide may be reacted with methanol and an acid to form a glucuronide methylester (glucuronide-mE). The liposome can be prepared with an internal pH greater than 7 and an external pH of less than 7. The liposome may be prepared with an internal pH from 7.5 to 8.5. The liposome can then be contacted with a solution comprising glucuronide-mE and having a pH from 4.5 to 5.5. The liposome can then be purified from the solution. The internal pH of the liposome can be about 8 and the external pH of the liposome can be about 5. Alternatively, the internal pH of the liposome can be 8 and the external pH can be 5.

In the above aspects, liposomes may be prepared containing an internal high concentration of glucuronides sufficient to achieve a therapeutically effective dose. The liposomes can be produced with an externally low and internally high pH gradient. Without wishing to be bound by theory, a fundamental strategy of this method is based on an encapsulation mechanism that operates through at least the following two steps: 1. Loading of glucuronide-methylester (-mE) and 2. Internal saponification (hydrolysis) of the ester group for intraliposomal production and trapping of glucuronides.

A glucuronide-mE can be significantly more membrane permeable than its corresponding glucuronide, which allows for a substantially increased number of glucuronide-mE molecules to be loaded into a liposome versus the number of its corresponding glucuronide molecules. Without wishing to be bound by theory, the kinetics of loading into a liposome can depend on the partition of a molecule into the lipid bilayer of the liposome. A glucuronide with limited partition in the lipid bilayer may tend to remain outside of the liposome as its partition ratio between the aqueous solution outside of the liposome and the lipid bilayer may be very high. However, the methylester form of that glucuronide (glucuronide-mE) can more readily enter the lipid bilayer and transfer to the aqueous phase within the liposome that is surrounded by the lipid bilayer of the liposome.

It can be advantageous to have the aqueous phase inside the liposome to be at a high pH. The high pH allows for the ester group on the glucuronide-mE to be rapidly hydrolyzed through a mechanism known as saponification. This hydrolysis from glucuronide-mE to the corresponding glucuronide can drive the equilibrium of the glucuronide-mE from the lipid bilayer to the aqueous phase inside the liposome. Further, the corresponding glucuronide may have much more limited solubility in the lipid bilayer versus the glucuronide-mE, as previously discussed, and as such the glucuronide would tend to remain within the liposome rather than crossing the lipid bilayer to the aqueous phase outside of the liposome.

A glucuronide-mE can be synthesized by dissolving a glucuronide in methanol with an acid catalyst without the need of any particular chemistry skills or equipment. The reaction can be conducted at a temperature between 50 and 70° C., for example 60 to 65° C. The reaction may be monitored by chromatographic means, for example HPLC. The reaction time can be one hour or longer. Purification can be undertaken to purify out the glucuronide methylester from the acid catalyst. The glucuronide methylester can be purified by HPLC using a C18 reverse phase column and washing with 5% methanol in water. During this washing step, glucuronide-mE remains trapped by the column. The glucuronide-mE can be subsequently eluted with 100% methanol or nearly 100% methanol. Rotary evaporation, lyophilization, or any other drying means can be used to remove the methanol from the glucuronide-mE.

Figure 1:
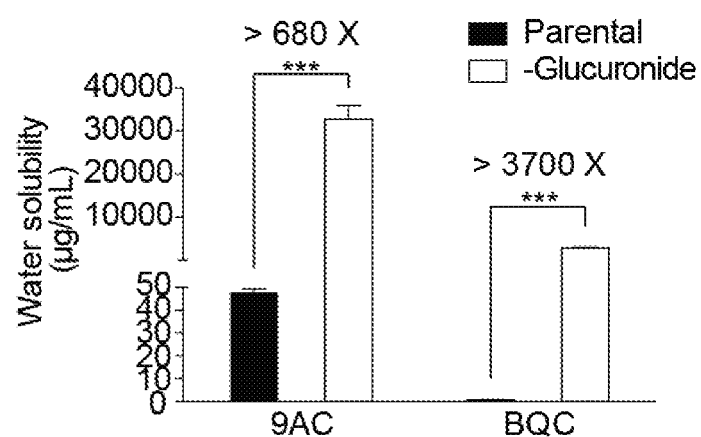
FIG. 1 illustrates the increase in water solubility after conjugation of a glucuronide group to hydrophobic drugs. (Abbreviations: 9AC, 9-aminocamptothecin; BQC, 5,6-dihydro-4H-benzo[de]quinoline camptothecin) n=3. Error bars, SD. Two-tailed unpaired Student's T-test was used for statistical analysis. Stars indicate significance; $p<0.0001$ (***)

The conjugation of a glucuronide residue dramatically increases the water solubility of the parental compound (FIG. 1), suggesting better retention in liposomes.

Figure 2:
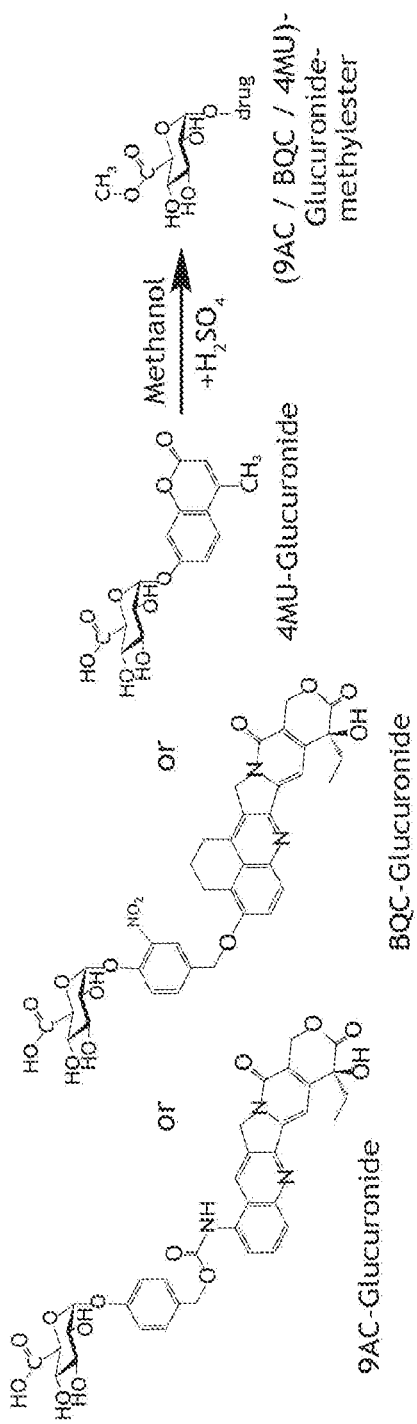
FIG. 2 illustrates the synthesis of glucuronide methylesters (-mE) from glucuronides. Chemical synthesis of 9-aminocamptothecin glucuronide (9AC-G), 5,6-dihydro-4H-benzo[de]quinoline camptothecin glucuronide (BQC-G) and 4-methylumbelliferyl glucuronide (4MU-G) to glucuronide methylesters (-mE) was achieved in methanol and acidic condition by addition of $H_2SO_4$.
Figure 3:
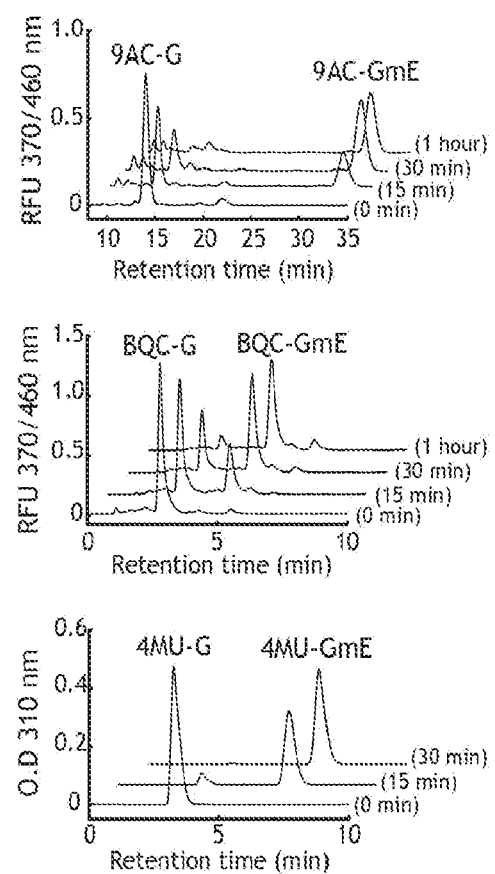
FIG. 3 shows the time-dependent formation of glucuronide-mE from glucuronides at 65° C. in acidic methanol. Results were obtained by high performance liquid chromatography (HPLC). (RFU=relative fluorescent units).
Figure 4:
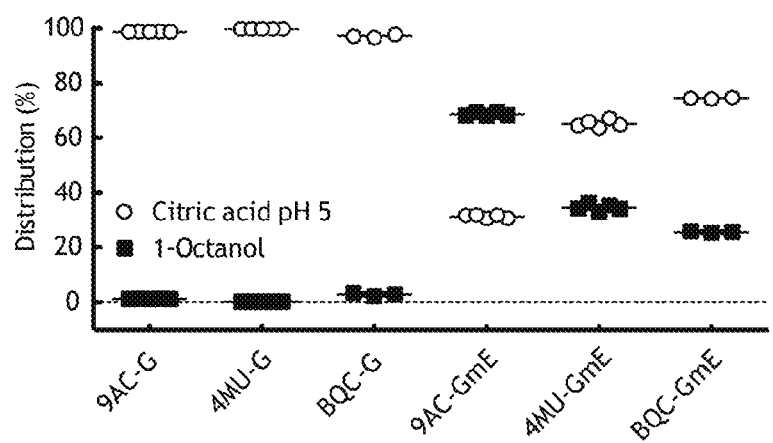
FIG. 4 illustrates the octanol to water distribution of glucuronides and glucuronide-mE. Glucuronides and glucuronide-mE were incubated overnight in immiscible aqueous and organic phases (citric acid pH 5 and 1-octanol) under gentle shaking at room temperature. Samples from each phase were analyzed to characterize the distribution of the compounds. n=3-5
Figure 5:
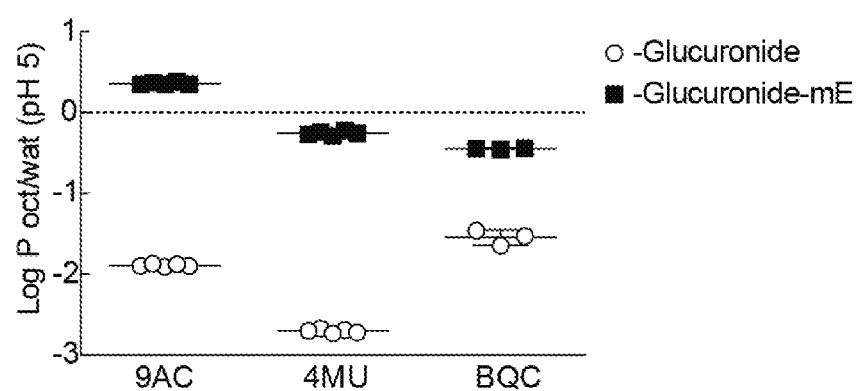
FIG. 5 illustrates the Log P of glucuronides and glucuronide-mE compounds in each phase of 1-octanol and citric acid pH 5 following the formula: $\log P_{octanol/water} = \log ([solute]_{octanol}/[solute]_{water})$. n=3-5. Error bars, SD

9-aminocamptothecin glucuronide (9AC-G), 5,6-dihydro-4H-benzo[de]quinoline-camptothecin-β-D-glucuronide (BQC-G) and 4-methylumbelliferyl-β-D-glucuronide (4MU-G) can be incubated in methanol in the presence of a strong acid (sulfuric acid) as a catalyzer (FIG. 2). After 1 hour at 65° C. most of the glucuronides (9AC-G, BQC-G and 4MU-G) are converted to glucuronide-mE (9AC-GmE, BQC-GmE and 4MU-GmE) as demonstrated by high-pressure liquid chromatography, as shown in FIG. 3. Newly synthesized 9AC-GmE, BQC-GmE and 4MU-GmE display increased partition into an organic phase as compared to 9AC-G, BQC-G and 4MU-G, respectively, in an octanol-to-water partitioning assay, as shown in FIG. 4 and FIG. 5. This result indicates that methylester modification can increase the solubility in lipid membranes and increase active loading efficiency.

Figure 6:
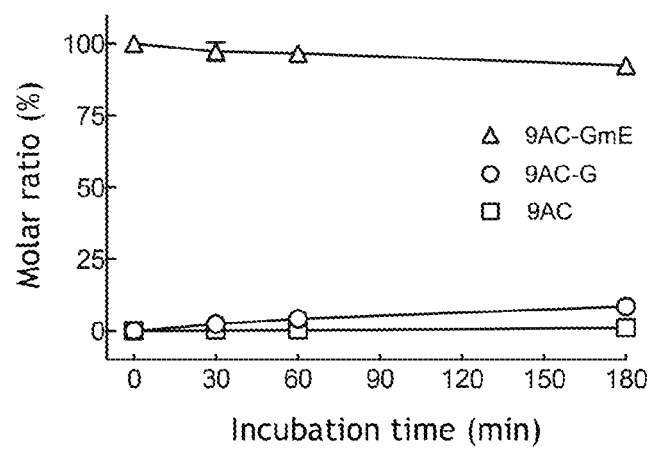
FIG. 6 illustrates the stability of 9-aminocamptothecin glucuronide methylester (9AC-GmE) at acidic pH. 9AC-GmE stability was monitored over time at 75° C., at pH 5. Quantification was done by HPLC at excitation and emission of 370 and 460 nm, respectively. (Abbreviations: 9AC, 9-aminocamptothecin; 9AC-G, 9-aminocamptothecin glucuronide; 9AC-GmE, methylester form of 9AC-G). n=3. Error bars, SD.
Figure 7:
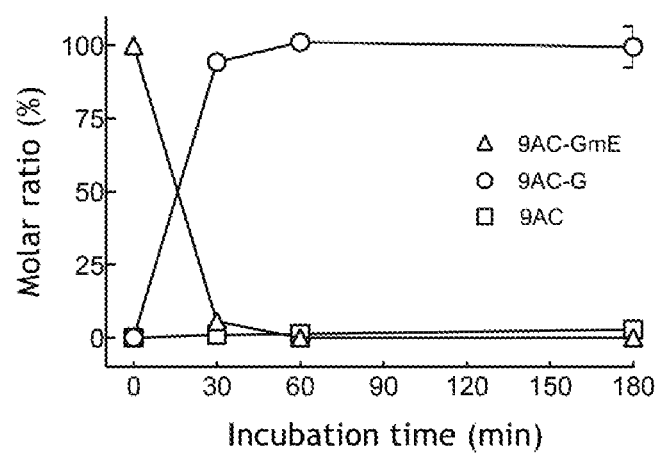
FIG. 7 illustrates the conversion of 9-aminocamptothecin glucuronide methylester (9AC-GmE) to 9-aminocamptothecin glucuronide (9AC-G) at basic pH. 9AC-GmE conversion to 9AC-G was monitored over time at 75° C., at pH 8.5. Quantification was done by HPLC at excitation and emission of 370 and 460 nm, respectively. n=3. Error bars, SD.

The methods described herein may further involve use of a derivative compound, where the carboxylic acid group of the glucuronic residue is replaced by a methylester to produce a glucuronide-mE which has significantly increased membrane permeability. Their loading in liposomes at low external pH, at which the glucuronide-mE is stable (FIG. 6) can allow for high drug-to-lipid ratios. Without wishing to be bound by theory, the internal high pH helps the spontaneous hydrolysis of the methylester to produce internal glucuronide by heating for about 1 hour (FIG. 7). By using this method, glucuronides can be stably encapsulated at very high drug-to-lipid ratios, where conventional weak acid loading methods would fail to encapsulate effective amounts.

Figure 8:
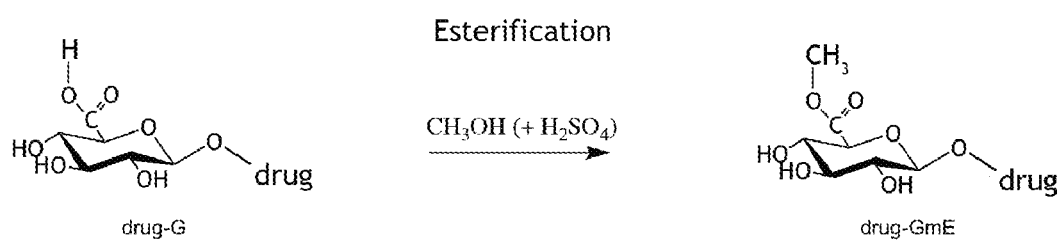
FIG. 8 illustrates the production of the glucuronide-mE in methanol and sulfuric acid ($H_2SO_4$) at 65° C.
Figure 9:
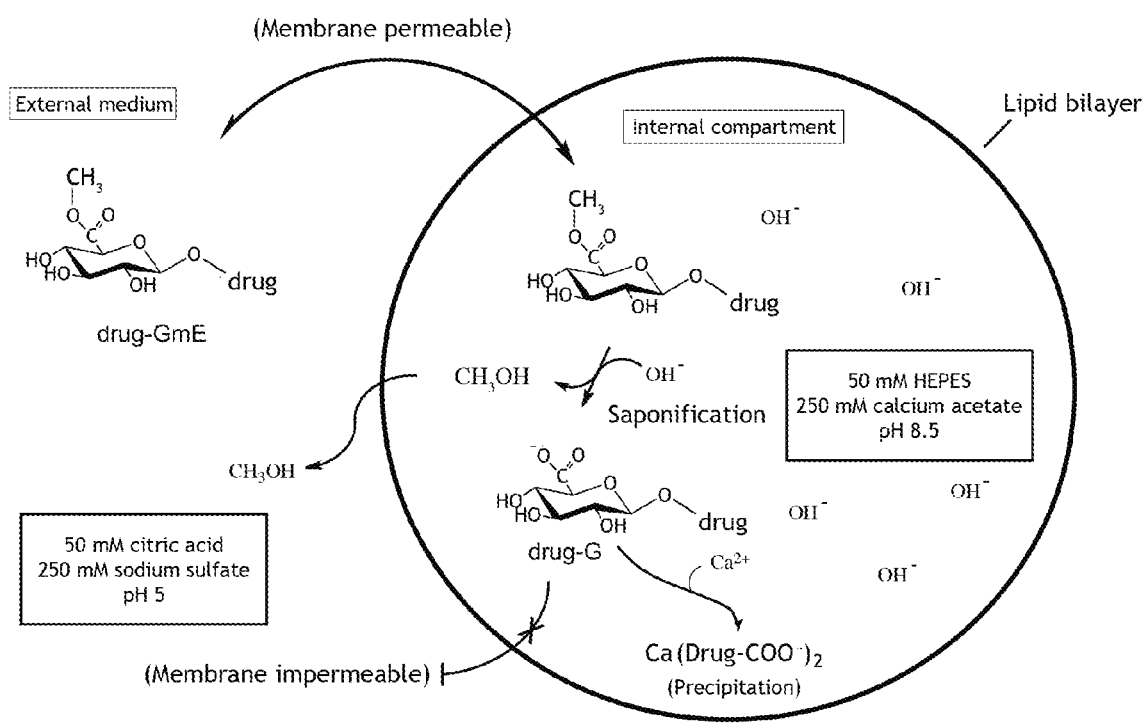
FIG. 9 illustrates the proposed loading mechanism of a glucuronide-mE drug derivative and intraliposomal conversion to a glucuronide drug derivative. The glucuronide-mE is added to the liposome external medium. At pH 5 and 75° C., glucuronide-mE is stable outside the liposomes but can permeate the lipid bilayer of the liposomes. Inside the liposomes, free hydroxide ions at the internal higher pH react with glucuronide-mE, releasing methanol ($CH_3OH$) and the glucuronide form of the derivative through saponification. The ionized glucuronide can precipitate with calcium ions inside the liposome.

FIG. 8 describes the formation of a glucuronide-mE in acidic methanol from a glucuronide. FIG. 9 describes a theoretical mechanism for glucuronide-mE (drug-GmE) in the external medium to pass through the lipid bilayer of liposomes and conversion of the glucuronide-mE to a glucuronide (drug-G) under the high pH inside the liposomes. The high hydroxide ion concentration inside the liposomes can destabilize the methylester bond, releasing methanol while reforming a glucuronide form of the drug. The methanol can diffuse out of the liposomes but the internally formed glucuronide is hydrophilic and cannot easily diffuse across the lipid bilayer of the liposomes. The glucuronide drug derivatives may also form precipitates with the high concentrations of calcium ions inside the liposomes to remain stably encapsulated in the liposomes.

Figure 10:
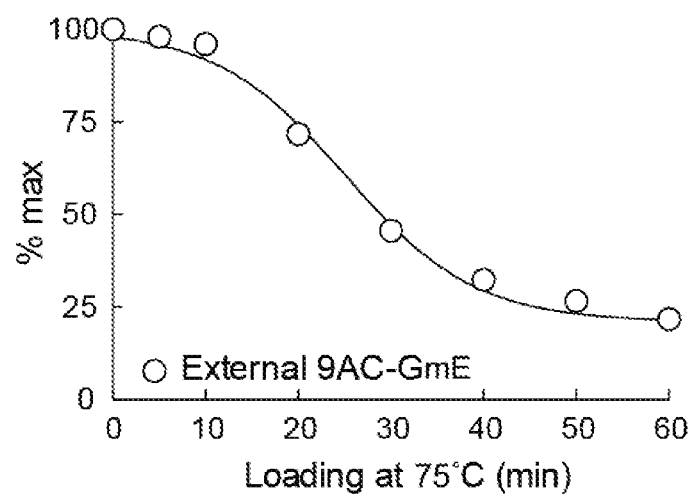
FIG. 10 illustrates the disappearance of 9AC-GmE in the external medium after mixing with liposomes having an external low pH and internal high pH at 75° C. prepared as described on FIG. 9.
Figure 11:
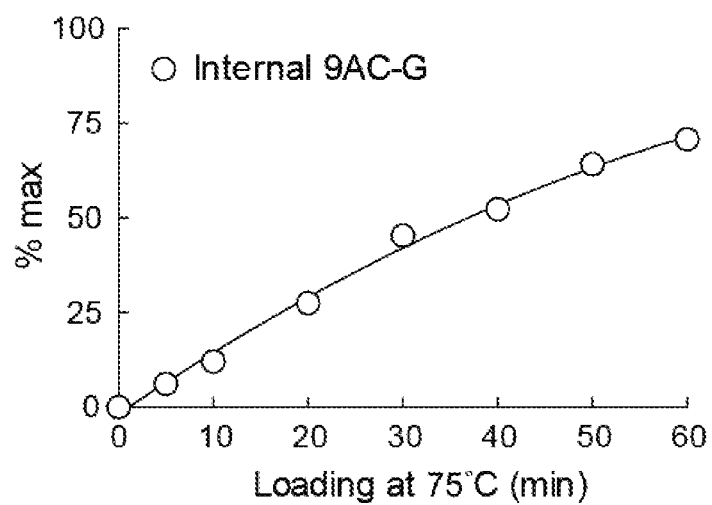
FIG. 11 illustrates the appearance of 9AC-G inside the liposomes after mixing the liposomes with 9AC-GmE at 75° C.

FIG. 10 demonstrates the effect of the addition of a glucuronide-mE in the external medium of liposomes described in FIG. 9. At elevated temperature, a disappearance of 9AC-GmE was observed in the external medium of the liposomes, suggesting that the methylester form of the glucuronide is being loaded inside the liposomes by crossing through the liposome membrane. In FIG. 11, the corresponding hydrophilic glucuronide (9AC-G) is appearing inside liposomes over time, due to the saponification of the loaded 9AC-GmE.

Figure 12:
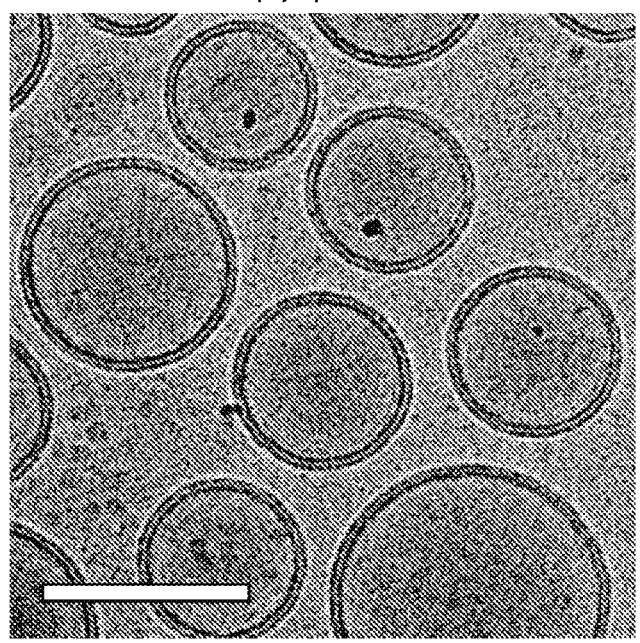
FIG. 12 illustrates the imaging of liposomes by cryogenic electron microscopy before drug loading. (Scale bar=100 nm).
Figure 13:
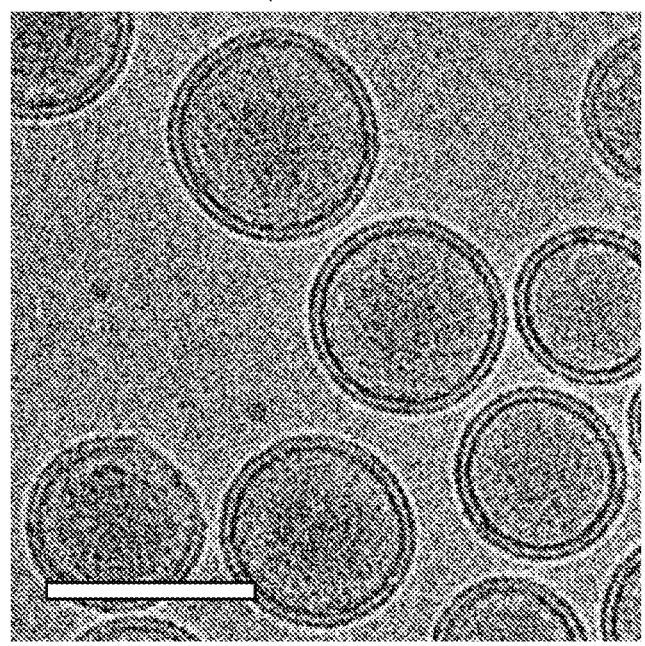
FIG. 13 illustrates the imaging of liposomes by cryogenic electron microscopy after loading with 9-aminocamptothecin (9AC). (Scale bar=100 nm).
Figure 14:
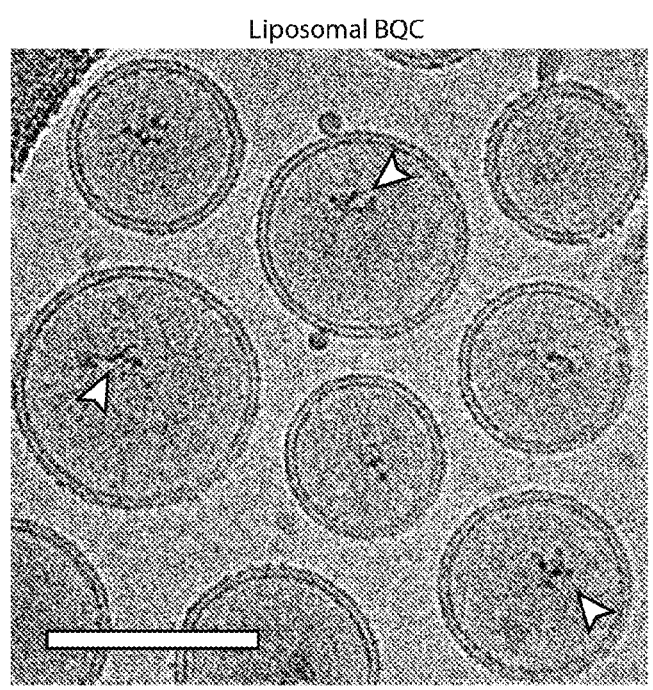
FIG. 14 illustrates the imaging of liposomes by cryogenic electron microscopy after loading with 5,6-dihydro-4H-benzo[de]quinoline camptothecin (BQC). Arrows show precipitated internal BQC (Scale bar=100 nm).
Figure 15:
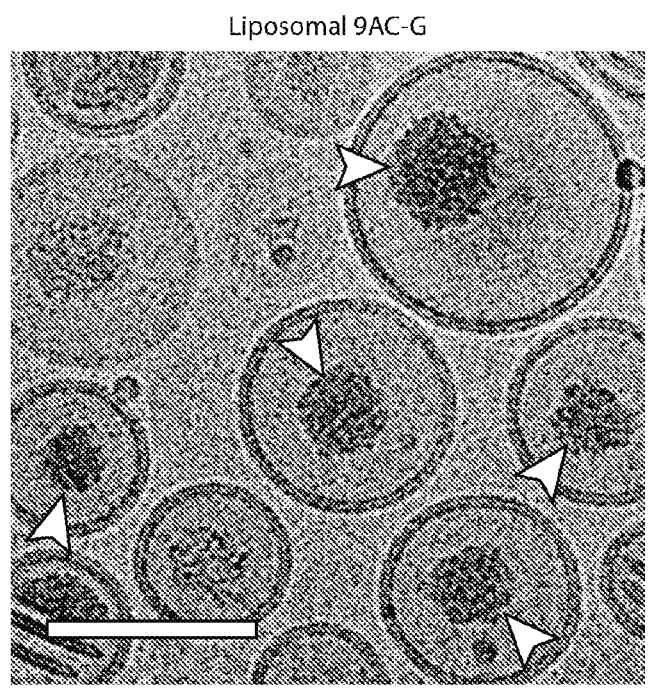
FIG. 15 illustrates the imaging of liposomes by cryogenic electron microscopy after loading with 9-aminocamptothecin glucuronide methylester (9AC-GmE) and internal conversion to 9AC-G. Arrows show precipitated internal 9AC-G. (Scale bar=100 nm).
Figure 16:
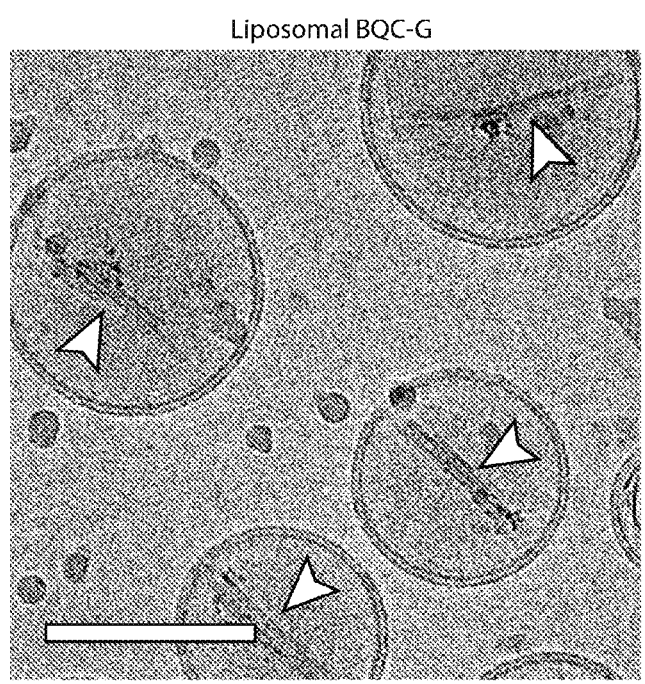
FIG. 16 illustrates the imaging of liposomes by cryogenic electron microscopy after loading with 5,6-dihydro-4H-benzo[de]quinoline camptothecin glucuronide methylester (BQC-GmE) and internal conversion to BQC-G. Arrows show precipitated internal BQC-G. (Scale bar=100 nm).

Compared to empty liposomes (FIG. 12), the visualization of the internal accumulation and retention of glucuronides inside the liposomes can be observed by cryogenic electron microscopy, such as in FIG. 15 (9AC-G) and FIG. 16 (BQC-G). Parental compounds 9AC and BQC were also loaded in liposomes of a same formulation as the ones used for the loading of 9AC-G and BQC-G. The loading principle here relies on the pH dependent lactone—carboxylic acid equilibrium. At low pH, the lactone rings of 9AC and BQC is closed, allowing a more lipophilic form to enters the liposomes. At internal alkaline pH, the lactone ring opens to form a carboxylic acid group, which can precipitate with internal calcium ions. FIG. 13 and FIG. 14, respectively show the liposomes after loading of parental 9AC and BQC. This observation demonstrates that loading 9AC and BQC under a glucuronide form helps to enhance the core accumulation and internal precipitation of these drugs.

There are many applications of the encapsulated compounds. The anti-cancer drug industry would benefit from the encapsulation of glucuronidated anticancer drugs for maximizing the drug delivery to tumor and safety for patients. Camptothecins are a family of well-known antineoplastic drugs, and their glucuronide derivatives can decrease their toxicity and increase their specificity. Moreover, glucuronide SN38 (SN38-G) is a metabolite of CPT-11, in use for the treatment of colorectal cancer patients. Encapsulation of SN38-G in liposomes might be of tremendous interest for the anticancer drugs industry. Particularly insoluble drugs such as paclitaxel or MMAE could be loaded in the core of the liposomes under glucuronidated form, instead of interacting with the liposomes bilayer. This could result in a better stability and safety of drug delivery.

Glucuronide-mE can be stable at a pH between 4 and 6, for example pH 5. The methylester group on the glucuronide-mE can be hydrolyzed at basic pH by saponification. The saponification can be undertaken within a liposome where the pH of the interior of the liposome is basic so as to reform the glucuronide within the liposome.

Liposomes can be prepared by any number of means. The liposome may comprise phosphocholine lipids. The liposome may comprise phosphoethanolamines. The liposome may also comprise cholesterol. The pH of the liposome can be regulated by the pH of a buffer used to rehydrate a dried lipid film prepared with lipid components of the liposome. Size exclusion chromatography undertaken at a certain pH different from that of the interior of the liposome can then be used to select for liposomes with a desired pH gradient. The pH of the liposome interior can be more than 7, for example, pH 7, 8, or 9 and the pH of the external buffer can be less than 7, for example, 4, 5, or 6. Dynamic light scattering may be used to measure the average diameter of liposome particles. Glucuronide-mE can be loaded into liposomes with an external pH that is lower than the internal pH.

Figure 17:
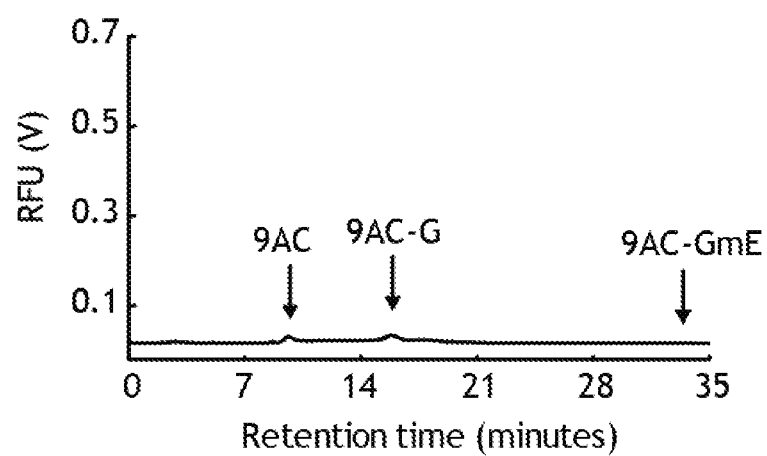
FIG. 17 illustrates the HPLC analysis of loaded liposomes. 9AC-GmE was added to the external medium of liposomes, loaded for 1 hour at 75° C., and non-encapsulated residue was removed by size exclusion chromatography. The figure shows the chromatogram of the liposomes directly injected to the column without lysis. (RFU=relative fluorescent units).
Figure 18:
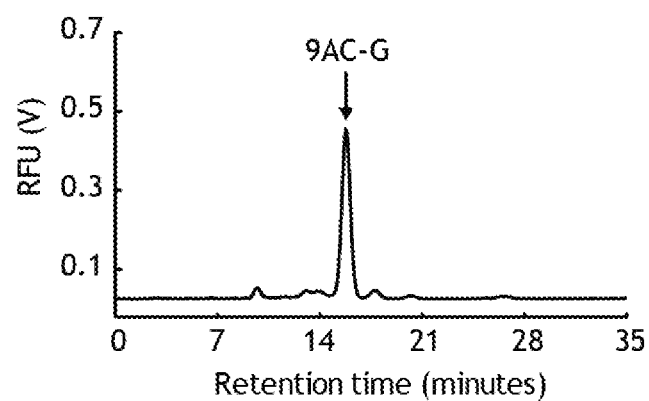
FIG. 18 illustrates the HPLC analysis of loaded liposomes. 9AC-GmE was added to the external medium of liposomes, loaded for 1 hour at 75° C., and non-encapsulated residue was removed by size exclusion chromatography. The figure shows the chromatogram of the liposomes directly injected to the column with lysis by 1% Triton X-100. (RFU=relative fluorescent units).

Glucuronide-mE can be incorporated into liposomes by first preincubating glucuronide-mE and liposomes separately at a temperature between 60-80° C. for 5-15 minutes, for example at 75° C. for 10 minutes, and then mixing them for a period of time, such as one hour, with some degree of gentle shaking, to allow glucuronide-mE loading and internal saponification to glucuronide. Size exclusion chromatography can be used to remove glucuronide-mE that remains outside of the liposomes. HPLC can be further undertaken on a sample of loaded liposomes diluted in detergent so as to assay the glucuronide-mE loading efficiency and conversion to glucuronide. FIG. 17 represents the HPLC analysis of 9AC-G loaded liposomes injected without use of a detergent to lyse the liposomes. No drug in the external medium is observed. FIG. 18 represents a HPLC analysis of the same liposomes after lysis with a detergent. Loaded 9AC-G is released after lysis and observed on the chromatogram.

Without wishing to be bound by theory, glucuronide-mE are stable outside of the liposomes in a weak acid environment (such as pH 5) and can interact with lipid bilayers due to an improved solubility in organic environments. Eventually, glucuronide-mE will migrate from the external to the internal environment of the liposome. Exposure to a relatively high pH (such as pH 8.5) within the liposome can lead to rapid hydrolysis of the methylester group on the glucuronide-mE to generate glucuronides in the internal environment of the liposome. These glucuronides may have a substantially lower ability to interact with the liposome lipid bilayer and thus would migrate from the internal to the external environment of the liposome at a substantially lower rate than that of a glucuronide-mE.

Figure 19:
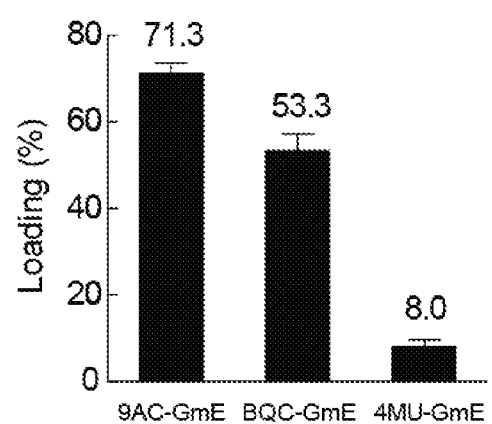
FIG. 19 illustrates the loading of glucuronide-mE. The loading capability of 9AC-GmE, BQC-GmE and 4MU-GmE (starting at 1:5 weight ratio, drug:lipid) were characterized by HPLC analysis of drug disappearance in the external medium. n=3, Error bars, SD.
Figure 20:
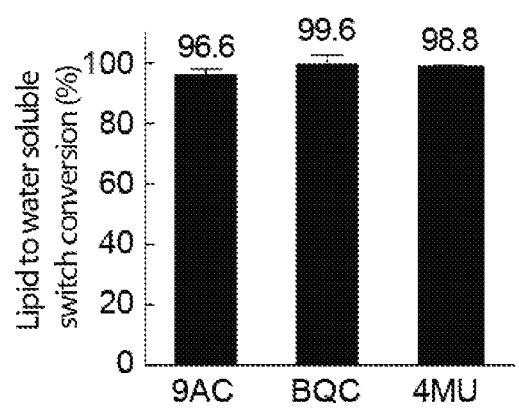
FIG. 20 illustrates the internal conversion of glucuronide-mE. The internal conversion by saponification of 9AC-GmE to 9AC-G, BQC-GmE to BQC-G and 4MU-GmE to 4MU-G, were characterized by HPLC after external drug was removed and loaded liposomes were lysed with Triton X-100 to analyze their contents. n=3, Error bars, SD.
Figure 21:
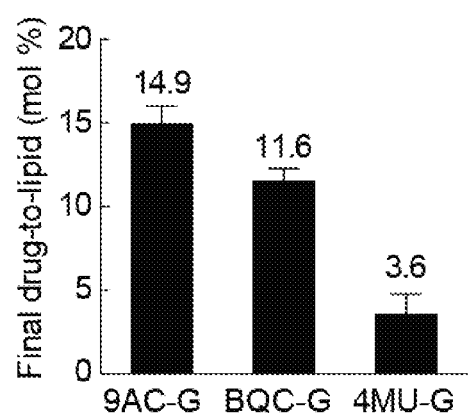
FIG. 21 illustrates the final drug-to-lipid molar ratio for glucuronide derivatives loaded as glucuronide methylesters. The final drug-to-lipid ratios were characterized by HPLC to determine the final content of internal glucuronide, and lipid amounts were determined by Bartlett's phosphorus assay. n=3, Error bars, SD.

FIGS. 19, 20 and 21 describe the loading, internal conversion of glucuronide-mE to glucuronide, and final drug-to-lipid molar ratio, respectively, for parental drugs 9-aminocamptothecin (9AC), 5,6-dihydro-4H-benzo[de]quinoline-camptothecin (BQC) and 4-methylumbelliferyl (4MU).

Methylesterification can be used to substantially increase the loading capacity of glucuronides into liposomes. It is possible to achieve a 5-fold increase in loading capability, a 10-fold increase, a 15-fold increase, a 20-fold increase, a 25-fold increase, a 30-fold increase, a 35-fold increase, a 40-fold increase or a 45-fold increase, and over 275 folds increase as was demonstrated in FIG. 22, of the glucuronide by practicing any of the methods described herein that include methylesterification of a glucuronide and loading the methylester into a liposome having an internal pH higher than that of the external environment.

In another aspect is provided a liposome comprising a glucuronide of an anticancer drug. The liposome can be prepared by a process comprising adding a methylester form of the glucuronide to a precursor liposome in a solution with an external pH, and with the liposome having an internal pH that is greater than the external pH. The liposomes internal pH is sufficiently high to convert the methylester form of the glucuronide to the glucuronide. The internal pH can be greater than 7 and the external pH can be less than 7. The internal pH can be from 7.5 to 8.5 and the external pH can be from 4.5 to 5.5. The internal pH can be about 8 and the external pH can be about 5. The internal pH can be 8 and the external pH can be 5.

Figure 23:
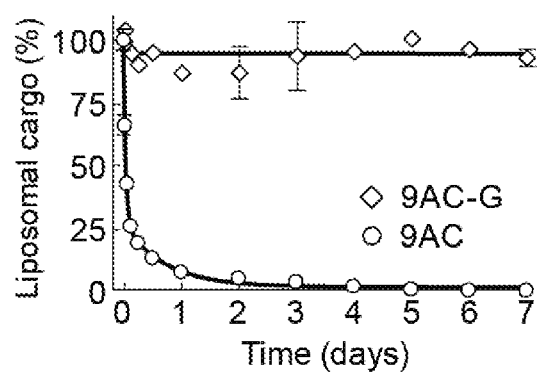
FIG. 23 illustrates the drug retention in liposomes when incubated at 37° C. in PBS containing 10% FBS. Curves show the comparison of the retention between parental 9AC and 9AC-G over a period of 7 days. n=3, Error bars, SD
Figure 24:
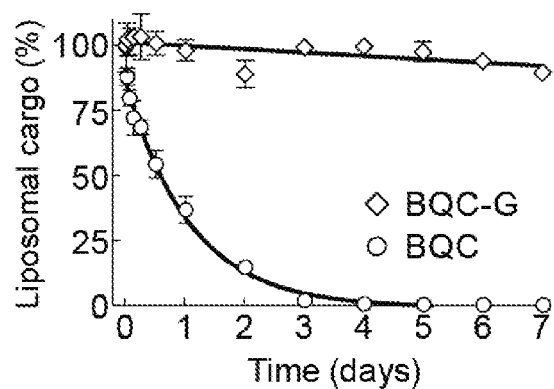
FIG. 24 illustrates the drug retention in liposomes when incubated at 37° C. in PBS containing 10% FBS. Curves show the comparison of the retention between parental BQC and BQC-G over a period of 7 days. n=3, Error bars, SD.

The liposomes provided in this aspect can be used in a method of treating cancer or reducing the size of a tumor by administering to a mammal or a human patient in need of treatment these liposomes comprising a glucuronide of an anticancer drug. Alternatively, liposomes loaded according to any of the aspects and embodiments described herein can be used to treat cancer or to reduce tumor size by administering to a mammal or a human patient in need of treatment such liposomes. The cancer may be lung cancer, breast cancer, ovarian cancer, prostate cancer, liver cancer, bladder cancer, cervical cancer, gastric cancer, head and neck cancer, melanoma, pancreatic cancer, renal cell cancer or colon cancer. The tumor may have origin from any organ, in particular lung, breast, ovaries, stomach, kidney, liver or colon. Various anticancer drugs can be used. The anticancer drug can be one or more of 4-methylumbelliferone, 9-aminocamptothecin, 5,6-dihydro-4H-benzo[de]quinoline-camptothecin, aclarubicin, actinomycin, amsacrine, bendamustine, bexarotene, betulin, bicalutamide, bleomycin, bortezomib, bosutinib, busulfan, cabazitaxel, cabozantinib, capecitabine, carboplatin, carmustine, chlorambucil, cisplatin, cladribine, cobimetinib, cyclopamine, cyclophosphamide, cytarabine, dacarbazine, dactinomycin, dasatinib, daunorubicin, decitabine, diaziquone, docetaxel, doxorubicin, enzalutamide, epirubicin, erlotinib, estramustine, etoposide, floxuridine, fludarabine, fluorouracil, fotemustine, hydroxyaniline mustard, hydroxyurea, gefitinib, gemcitabine, ibrutinib, idarubicin, ifosfamide, imatinib, irinotecan, ixabepilone, lapatinib, lenalidomide, letrozole, leucovorin, lomustine, mechlorethamine, melphalan, merbarone, mercaptopurine, mesna, methotrexate, mitomycin, mitoxantrone, mitozolomide, monomethyl auristatin, nedaplatin, nelarabine, nilotinib, nilutamide, N-nitroso-N-methylureaoxaliplatin, novobiocin, omacetaxine, paclitaxel, panobinostat, pazopanib, pemetrexed, pentostatin, plicamycin, pomalidomide, ponatinib, prednisolone, PR-104A, pyrrolo[2,1-c][1,4]benzodiazepine, quercetin, raltitrexed, regorafenib, romidepsin, ruxolitinibm, semustine, SN-38, sonidegib, sorafenib, streptozotocin, suberoylanilide hydroxamic acid, sunitinib, tamibarotene, tamoxifen, tarcedinaline, tegafur, temsirolimus, thiotepa, teniposide, topotecan, triptorelin, trabectedine, vandetanib, vemurafenib, venetoclax, vincristine, vinflunine, vinorelbine, vinblastine, vindesine, vismodegib, vorinostat The drug retention between glucuronide and non-glucuronide drug can be assessed in a liposomal drug release assay. In this assay, the liposomes loaded either with parental drug (hydrophobic) or glucuronidated form (hydrophilic) are compared. The liposomes were dialyzed in a phosphate buffered saline (PBS) with 10% fetal bovine serum (FBS) at 37° C. to mimic physiological conditions. The drug that leaks out of the liposomes is lost by dilution in a 1000 folds larger volume. The drug that remained inside the liposomes was analyzed by HPLC for parental and glucuronidated forms of 9AC (FIG. 23) and BQC (FIG. 24). A stronger retention was achieved for the drugs loaded under a glucuronidated form.

Figure 25:
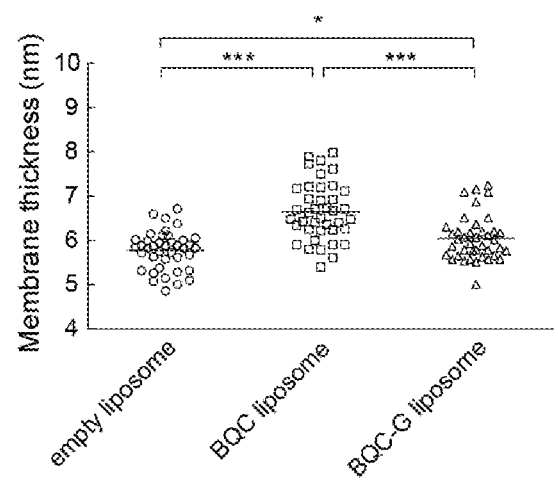
FIG. 25 illustrates the thickness of the membranes of liposomes loaded either with BQC or BQC-G. The thickness was measured based on micrographs obtained from cryogenic electron microscopy that were enlarged to their actual size in ImageJ (NIH). The amount of pixels corresponding to the 100 nm scale bar was determined using the "Set Scale" tool, prior to randomly measuring the membrane thickness at different positions of either empty liposomes or liposomes loaded with BQC or BQC-G. The randomization was obtained by overlapping a grid over the micrographs and thickness was measured each time the grid contacted with a liposomal membrane, until 40 values were collected. Two-tailed unpaired Student's T-test was used for statistical analysis. Stars indicate significance; $p<0.01$ (*) and $p<0.0001$ (***)
Figure 26:
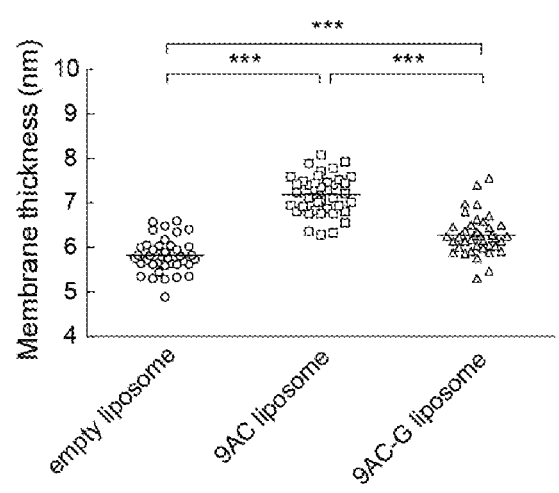
FIG. 26 illustrates the thickness of the membranes of liposomes loaded either with 9AC or 9AC-G. The thickness was measured based on micrographs obtained from cryogenic electron microscopy that were enlarged to their actual size in ImageJ (NIH). The amount of pixels corresponding to the 100 nm scale bar was determined using the "Set Scale" tool, prior to randomly measuring the membrane thickness at different positions of either empty liposomes or liposomes loaded with 9AC or 9AC-G. The randomization was obtained by overlapping a grid over the micrographs and thickness was measured each time the grid contacted with a liposomal membrane, until 40 values were collected. Two-tailed unpaired Student's T-test was used for statistical analysis. Stars indicate significance; $p<0.0001$ (***)

The membrane thickness of the liposomes was increased after loading of BQC (FIG. 25) and 9AC (FIG. 26). This also supports the idea that hydrophobic compounds accumulate in the membrane of the liposomes by hydrophobic interactions. This type of loading is considered to be unstable, and drug easily leaks out of the liposomes. Loading of 9AC-GmE and BQC-GmE to encapsulate 9AC-G and BQC-G, respectively, resulted in liposome membrane thicknesses that were closer to the membrane thickness of liposomes before drug loading, which suggest a shift in the tropism of the drugs from membranes to the liposome aqueous core.

Figure 27:
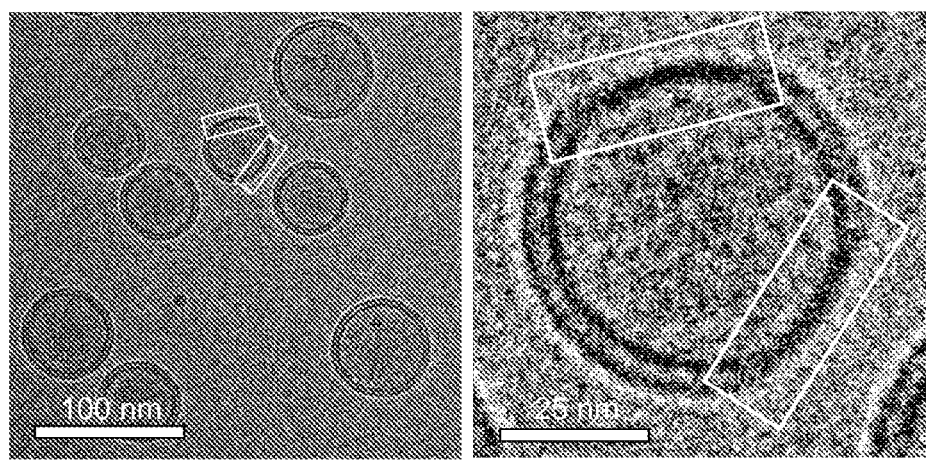
FIG. 27 illustrates the visualization of membrane defects after loading of 9AC in liposomes. The white boxes are placed in the areas where the membrane appears as a destabilized bilayer.

Membranes defects were observed in some liposomes loaded with 9AC that might result from the accumulation of 9AC in the liposome membrane (FIG. 27). Hydrophobic compounds tend to partition into the liposomes membranes where they interact with the lipid tails and sometimes destabilize the bilayer.

Figure 28:
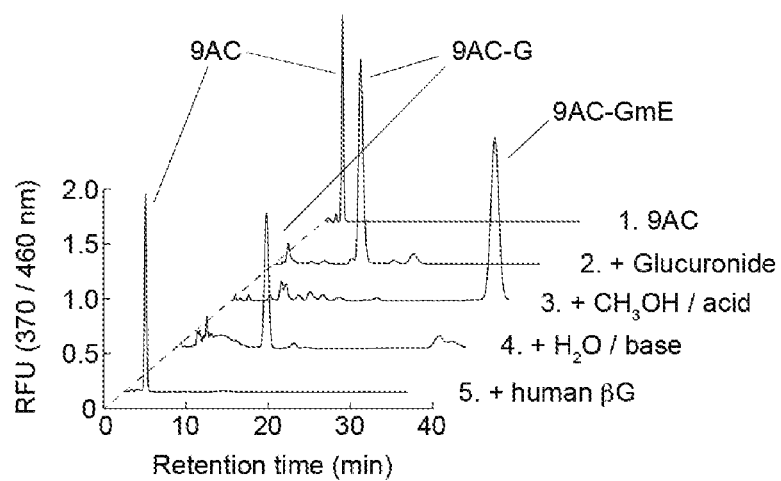
FIG. 28 illustrates the reversibility of the conjugation of the glucuronide residue to a parental compound. Here, 9AC was analyzed by HPLC before (1.) and after glucuronide conjugation (2.). After conjugation, 9AC-G was incubated in acidic methanol and showed complete conversion to 9AC-GmE (3.) and was switched back to 9AC-G in basic water (4.). 9AC-G incubated with human enzyme beta-glucuronidase at pH 4.5 to mimic the lysosomal conditions, could regenerate the original parental drug 9AC (5.). (RFU=relative fluorescent units)
Figure 29:
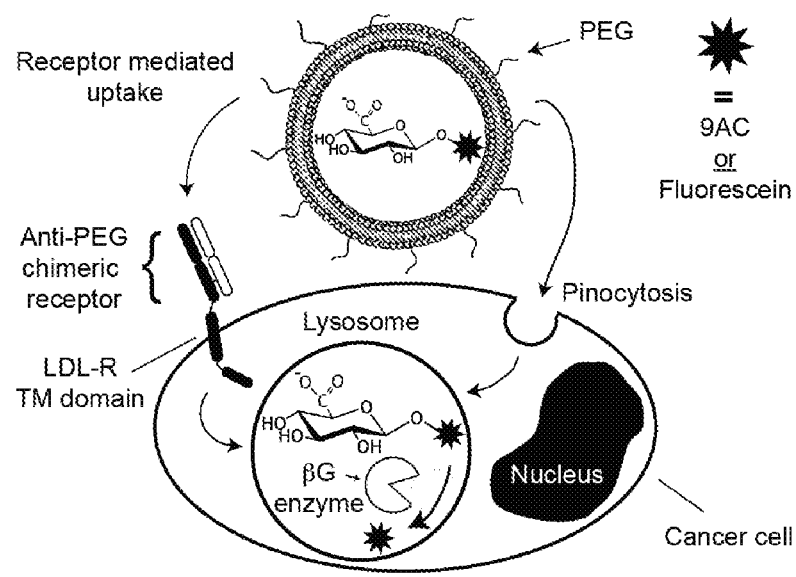
FIG. 29 represents a schematic illustration of the mechanism of cellular uptake, lysosomal degradation and drug reactivation in cancer cells. Some cells were engineered to express a chimeric receptor comprising the transmembrane domain of low density lipoprotein receptor (LDL-R) fused to an extracellular anti-PEG fragment antigen binding (Fab) antibody to demonstrate the importance of cellular uptake in parental drug regeneration. Cells that do not express the chimeric receptor (wild type) also can uptake the liposomes by a mechanism called pinocytosis. The liposomes contain either 9AC-G or fluorescein-di-glucuronide (fluorescein-di-G) for further analysis.
Figure 30:
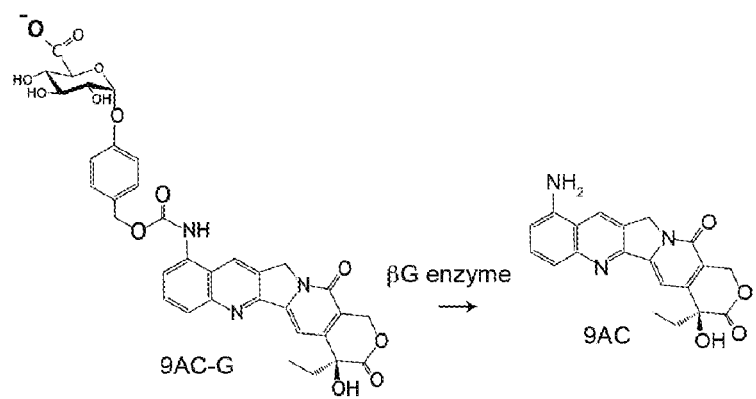
FIG. 30 illustrates the activation of 9AC-G to 9AC by lysosomal enzyme human beta-glucuronidase.
Figure 31:
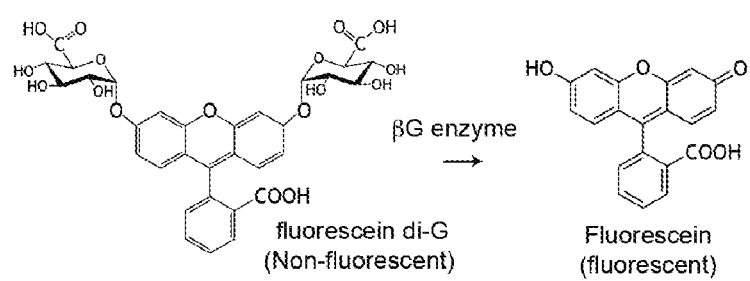
FIG. 31 illustrates the activation of fluorescein-di-G to fluorescein by lysosomal enzyme human beta-glucuronidase.
Figure 32:
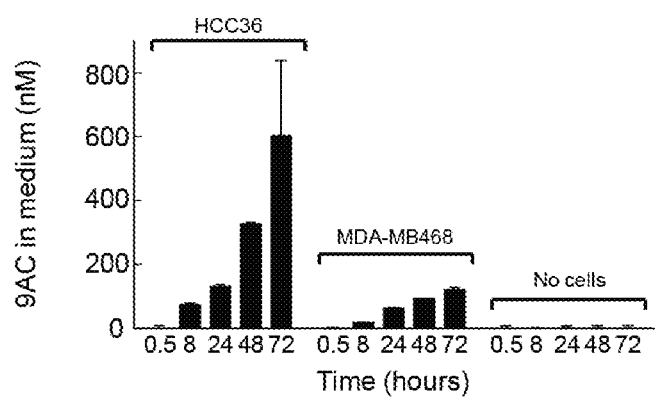
FIG. 32 illustrates the amount of 9AC in the medium of wild type HCC36 and MDA-MD468 human cancer cells over time after incubation with 9AC-G liposomes. 9AC was found in increasing amounts in the medium of both cells but not in control wells containing no cells. n=3, Error bars, SD
Figure 33:
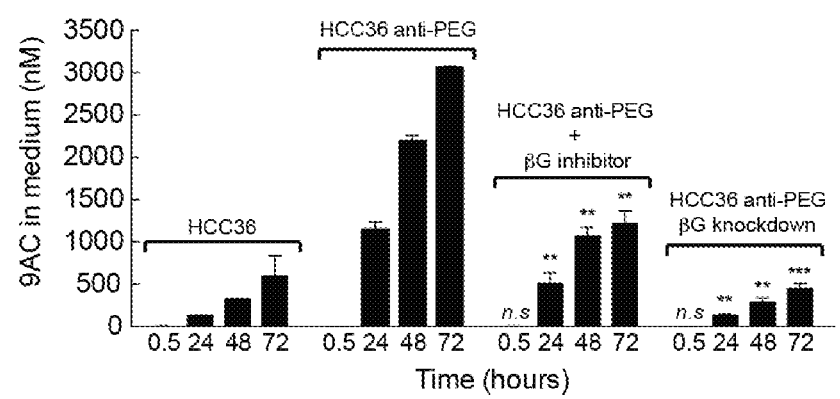
FIG. 33 illustrates the amount of 9AC in the medium of wild type HCC36 and HCC36 human cancer cells engineered to express chimeric LDL-R/anti-PEG receptors on their surface. Compared to wild-type cells, engineered cells (HCC36 anti-PEG) could generate more 9AC. When HCC36 anti-PEG cells were incubated with beta-glucuronidase inhibitor or when the expression of the enzyme was knocked down, the amount of 9AC produced was significantly reduced. n=3, Error bars, SD. Two-tailed unpaired Student's T-test was used for statistical analysis. Stars indicate significance; ns=non-significant, $p<0.001$ () and $p<0.0001$ (*). Statistical comparison is made against HCC36 anti-PEG cells at equivalent time points.
Figure 34:
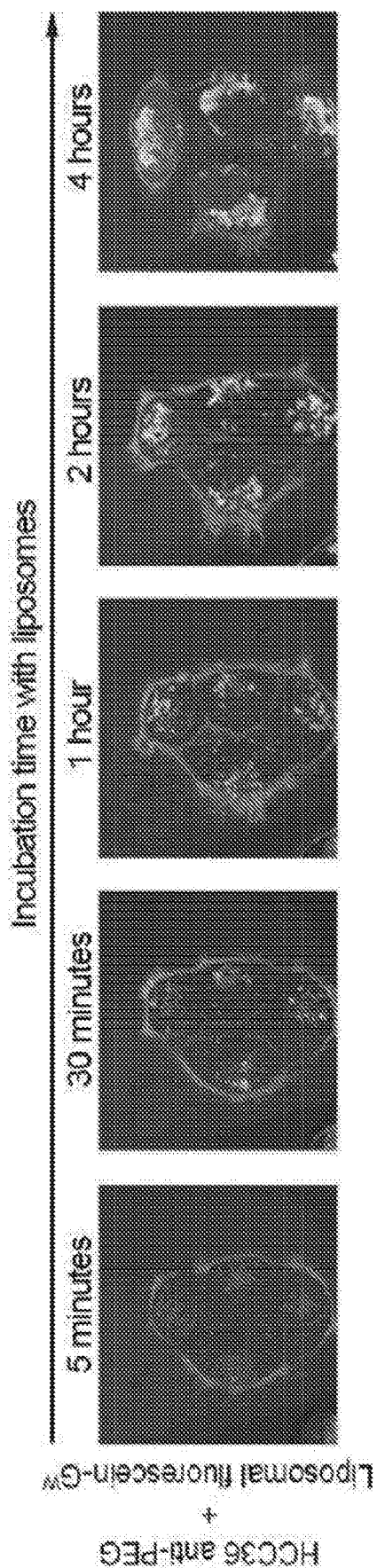
FIG. 34 illustrates the incubation of HCC36 anti-PEG cells with fluorescein-di-G liposomes. The activation of fluorescein-di-G (non fluorescent) to fluorescein (green)

Drugs conjugated to glucuronides can be regenerated to their parental form by a human lysosomal enzyme, beta-glucuronidase, as demonstrated in an in-vitro assay at pH 4.5 to mimic the pH in lysosomes. 9AC-G was completely converted to 9AC (FIG. 28). In real conditions, it is extrapolated that liposomal glucuronides can be uptake by cells and that the liposomes can release the glucuronide inside lysosomes after degradation as illustrated in FIG. 29. Illustrations of compound regeneration are provided using 2 examples: 9AC-G (linked by self-immolative chemical linker that is removed upon enzyme hydrolysis, FIG. 30) and fluorescein (directly linked to glucuronide residues, FIG. 31). Effective amounts of 9AC were found in the medium of HCC36 and MDA-MB468 human cancer cells after addition of 9AC-G liposomes. On the other hand, when no cells were present, no 9AC was found, meaning that the regeneration of 9AC was dependent on the cells (FIG. 32). When the uptake of liposomes into the cells was artificially increased by engineered low density lipoprotein receptor transmembrane domain (LDL-R TM) with anti PEG Fab extracellular domain, the amount of 9AC in the medium were significantly increased. When adding beta-glucuronidase inhibitor, or when reducing the amount of beta-glucuronidase expressed by gene knockdown, the amounts of 9AC produced were significantly decreased (FIG. 33). These results show that the regeneration of parental compound depends on cellular uptake and beta-glucuronidase. To further illustrate the parental compound regeneration ability, we incubated HCC36 cells engineered with LDL-R/anti PEG receptors with liposomal fluorescein-di-G (non-fluorescent). At early time, the liposomes (red) were taken up by the cells and started to colocalize with the lysosomes (magenta). Subsequently, the cell cytoplasm turned to green, demonstrating the activation of fluorescein-di-G to fluorescein (FIG. 34).

Anticancer activity of liposomes loaded with glucuronide-mE to encapsulate glucuronide can be assessed in-vitro or in-vivo. In an in-vitro assay, cancer cell lines can be seeded in wells or plates and various concentrations of liposomal glucuronide can be applied to the cells for a period of time, such as 24 hours, and cell killing can be assayed. Tritiated thymidine can be used to assay cell proliferation. In addition, human serum albumin binds to free 9AC-G and inactivates the drug, however, under a liposomal form, 9AC-G does not bind to human serum albumin and efficacy is not affected (FIG. 35 and FIG. 36). The data in FIG. 37 and FIG. 38 show the results of an in-vitro assessment of the toxicity of liposomal 9AC-G, compared to liposomal doxorubicin (Doxisome®) used here as a clinically validated liposomal drug. Liposomal doxorubicin and liposomal 9AC-G toxicities were assessed with 3 human colon cancer cells (LS174T, HT29, and HCT16), 3 human lung cancer cells (CL1-5, NCI-H2170, and SK-MES-1) and 1 human breast cancer cells (MDA-MB-468). For all cell lines, 9AC-G liposomes provided significantly better anti-proliferative activity against LS174T, HT29, HCT116, CL1-5, NCI-H2170 and MDA-MB-468 and equivalent anti-proliferative activity against SK-MES-1 when compared to doxorubicin liposomes. Liposomal drugs $IC_{50}$ were evaluated and summarized in Table 1.

Liposomes loaded with glucuronide can be administered to a mammal or a human patient who has cancer cells in need of killing. The cancer cells can for example be from lung, breast or colon, for example. The administration can occur intravenously. The degree of tumor reduction and/or the toxicity of the liposomes loaded with glucuronide can be assessed. Liposomes loaded with glucuronide can be effective to reduce tumor size.

Example 1: Synthesis of Glucuronide Methylesters (-mE) from Glucuronides 9-aminocamptothecin glucuronide (9AC-G) and 5,6-dihydro-4H-benzo[de]quinoline-camptothecin-β-D-glucuronide (BQC-G) were synthesized from parental compounds as previously described[20]. 4-methylumbelliferyl-β-D-glucuronide (4MU-G) was purchased from Sigma-Aldrich. (St. Louis, Mo.).

Glucuronide-mE derivatives of the 9AC-G, BQC-G and 4MU-G were synthesized by dissolving 25 mg of the glucuronides in 1 mL methanol with 3.5 μL of $H_2SO_4$ to act as catalysis. The solution was incubated at 60-65° C. and the reaction was monitored by HPLC by analyzing samples at different times (FIG. 3). The reaction was normally terminated after 1 hour. The glucuronide-mE forms of 9AC-G, BQC-G and 4MU-G (9AC-GmE, BQC-GmE and 4MU-GmE) were purified by HPLC to eliminate $H_2SO_4$ and residual glucuronides. 9AC-GmE, BQC-GmE and 4MU-GmE were loaded onto a hand-packed preparative column of LiChroprep® RP-18 (40-63 μm) (Merck, Germany) and washed with a mobile phase composed of 5% methanol in water. Under these washing conditions, glucuronides-mE are not eluted and remain trapped inside the column. Later, the mobile phase was shifted to 100% methanol and the eluent was collected. Pure 9AC-GmE, BQC-GmE and 4MU-GmE in methanol were dried under rotary evaporation and suspended in DMSO. The final concentration of each compound was determined by analytical HPLC and adjusted to 10 mg/mL.

Distribution of the different compounds were measured by dilution in a 1:1 volume of octanol and 100 mM citric acid buffer at pH 5 (FIG. 4). The solutions were gently stirred for 24 hours at room temperature, spun down at 2,500×g and glucuronides or glucuronide-mE in each phase was quantified by HPLC and the partition coefficients were calculated as log $P_{octanol/water}$=log ([solute]$_{octanol}$/[solute]$_{water}$) (FIG. 6).

HPLC analysis was performed using a reverse phase C18 column (Xbridge™ C18, 4.6×150 mm, 5 μm). Samples of 9AC, 9AC-G, 9AC-GmE, 4MU, 4MU-G and 4MU-GmE were run in a mobile phase composed of 24% acetonitrile and 30% acetonitrile for BQC, BQC-G and BQC-GmE at 2 mL/min. All mobile phases were adjusted to pH 2.9 with 25 mM citric acid (by addition of 10 N NaOH), degassed by sonication under vacuum, and filtered through a 0.2 m bottle top filter membrane (Nalgene® Rapid-Flow). Detection was performed with a fluorescence detector (Jasco FP-2020) at excitation/emission wavelengths of 370/460 nm for 9AC, 9AC-G, 9AC-GmE, BQC-G, BQC-GmE and 370/575 nm for BQC. 4-MU, 4MU-G and 4MU-GmE were detected with an U.V. detector (Jasco U.V. 975) at 310 nm. Data was collected and analyzed on Gold software (Beckman).

The behavior of 9AC-GmE was investigated at different pH and temperatures. What was observed was that 9AC-GmE is very stable at pH 5, but the methylester group easily is hydrolyzed at basic pH by saponification (FIGS. 6 and 7). Therefore the methylester group of 9AC-GmE is hydrolyzed at high pH to reform 9AC-G, demonstrating the reversibility of the reaction.

Example 2: Liposome Preparation

This example describes the preparation of liposomes composed of 1,2 distearoyl sn glycerol 3 phosphocholine (DSPC), 1,2 distearoyl sn glycerol 3 phosphoethanolamine [methoxy(polyethylene glycol) 2000] (DSPE-PEG2000) and cholesterol and having an interior pH of 8.5 and exterior pH of 5. Stock solutions of DSPC, DSPE-PEG2000 and cholesterol in chloroform were mixed at a 65:5:30 molar ratio and 10 mg total lipid amount. A dried lipid film was formed at 65° C. by rotary evaporation (Büchi, Rotavapor RII) and rehydrated with 250 mM calcium acetate, 50 mM HEPES buffer pH 8.5, at 65° C. to a final lipid concentration of 10 mg/mL. The liposomal suspension was submitted to 5 freeze/thaw cycles using liquid nitrogen followed by extrusion 21 times through 400, 200, and 100 nm polycarbonate membranes each, at 72° C. using a mini-extruder (Avanti Polar Lipids, Inc. Alabaster, Ala.) and transferred to ice. The pH gradient across the liposome membranes was obtained by size exclusion chromatography on Sephadex® G50 against 250 mM sodium sulfate, 50 mM citric acid pH 5. The resulting "ready-to-load" liposomes were stored at 4° C. for a maximum of 1 month before loading. The final lipid concentration was determined by Bartlett's phosphorus assay and the average diameter of the particles was measured by dynamic light scattering (Malvern Instruments Zetasizer Nano system).

According to these preliminary results, liposomes were formed by rehydrating a dry lipid film with 250 mM calcium acetate, 50 mM HEPES buffer adjusted at pH 8.5 to obtain liposomes with an internally and externally high pH environment. Later the external medium was exchanged with 250 mM sodium sulfate, 50 mM citric acid adjusted to pH 5 by size exclusion chromatography with Sephadex G50. At that stage, the resulting liposomes with high internal/low external pH were ready to be loaded with glucuronide-mE.

Example 3: Drug Loading of Liposomes

The liposomes prepared in example 2 were diluted to 4 mg/mL with 250 mM sodium sulfate, 50 mM citric acid pH 5. Glucuronide-mE prepared in example 1 was stored at 10 mg/mL in DMSO. In the following example, 2 mg of liposomes and 0.4 mg of glucuronide-mE were pre-warmed 10 minutes separately at 75° C. and mixed for 1 hour with occasional gentle shaking. Non-encapsulated glucuronide-mE was removed by size exclusion chromatography on Sephadex® G50 against Tris-based buffer (50 mM Tris-Cl, 150 mM NaCl pH 7.4). Loading efficiency and glucuronide-mE intraliposomal conversion to glucuronide was determined by HPLC after dilution of the liposomes in 1% Triton X-100, 25 mM citric acid at pH 2.9.

Glucuronide-mE are stable outside of the liposomes (pH 5) and can interact with lipid bilayers due to an improved solubility in organic environments. Glucuronide-mE will penetrate the liposome lipid bilayer from the external to the internal environment. Encapsulated glucuronide-mE are then exposed to an internally high pH (8.5) which rapidly hydrolyzes the methylester group to generate glucuronides.

After loading, the liposomes were lysed by a solution containing 1% triton X-100 in order to analyze by HPLC the nature of the drug encapsulated inside the liposomes. As revealed by the chromatogram in FIG. 17, non-lysed liposomes did not contain drug in the external medium, whereas Triton X-100 treated liposomes showed a release of 9AC-G (FIG. 18). Only traces of 9AC-GmE were detected on the chromatogram, demonstrating efficient intraliposome drug conversion of 9AC-GmE to 9AC-G.

The liposomes were imaged before loading of drugs (FIG. 12) and after loading of 9AC (FIG. 13) and BQC (FIG. 14). Images were also obtained after 9AC-GmE (FIG. 15) and BQC-GmE (FIG. 16) were loaded into liposomes and converted to 9AC-G and BQC-G inside the liposomes by the high internal pH. Images were obtained on Holey carbon film-covered 400-mesh copper grids (HC300-Cu, PELCO) glow-discharged in argon, oxygen-atmosphere for 10 seconds on the carbon side. A volume of 4 μL of liposomes (2 mg/mL) was pipetted onto the grids, blotted in 100% humidity at 20° C. for 3 seconds and plunge-frozen into liquid ethane cooled by liquid nitrogen using a Vitrobot (FEI, Hillsboro, Oreg.). Grids were then stored under liquid nitrogen and transferred to the electron microscope using a cryostage. Images of liposomes within the holes in the carbon film were obtained on a Tecnai™ F20 electron microscope (FEI) at 200 keV with 70 nm aperture. The low dose condition for each exposure was ~20 e$^-$/Å$^2$. Images were taken at 5 k and 50 k magnification and 2 to 3 nm defocus and recorded on a 4 k×4 k CCD camera (Gatan, USA).

Figure 22:
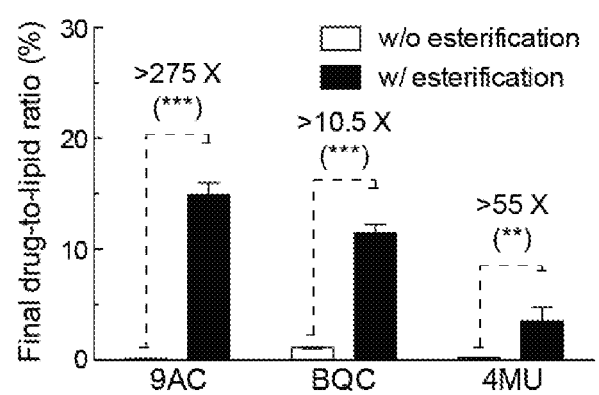
FIG. 22 illustrates a comparison of the loading performance of glucuronide derivatives or glucuronide methylester derivatives as well as the fold-improvement provided by drug glucuronide-mE as compared to drug glucuronides. n=3, Error bars, SD. Two-tailed unpaired Student's T-test was used for statistical analysis. Stars indicate significance; $p<0.001$ () and $p<0.0001$ (*).

In addition to 9AC-G and BQC-G, the liposomes were also loaded with 4-methylumbelliferyl-β-D-glucuronide (4MU-G) following the same procedure of esterification and intra-liposomal saponification. All these compounds were loaded under a glucuronide-mE form and converted inside the liposomes to glucuronides (FIGS. 19 and 20). Final drug-to-lipid molar ratios are shown in FIG. 21. An improvement of over 275 folds, 10.5 folds and 55 folds were achieved for 9AC, BQC and 4MU, respectively, when loaded under a glucuronide-mE form as compared to a glucuronide form (FIG. 22).

Example 4: Improved Drug Retention

Parental forms of 9AC and BQC were loaded into liposomes using the same liposomal formulation. At external low pH, hydrophobic 9AC and BQC are neutral and either interact with the liposome membranes or become negatively charged inside liposomes at high pH by reversible opening of their lactone ring to a slightly less hydrophobic carboxylate form. Liposomal 9AC, BQC, 9AC-G and BQC-G were dialyzed in PBS supplemented with 10% fetal bovine serum at 37° C. over a period of seven days. Glucuronide drug leakage from liposomes was significantly reduced compared to their hydrophobic parental drugs (FIGS. 23 and 24). Liposomal 9AC and BQC display a burst release behavior from their carrier of over 90%, 1 day, and 3 days after dilution, respectively. Liposomal BQC-G and 9AC-G were both able to retain over 80% of their cargo over a period of 7 days. This data shows that retention of hydrophobic drugs in liposomes is significantly improved after glucuronidation. In addition, the glucuronide loaded liposomes remained stable during storage at 4° C. in Tris-based buffer (TBS) over a period of several months.

To complement the drug retention assay, the toxicity of free 9AC-G and liposomal 9AC-G were tested against human liver cancer cells (HCC36) in the absence or presence of a 9AC-G inhibitor, human serum albumin (FIGS. 35 and 36). Our results shows that in the presence of human serum albumin, free 9AC-G toxicity is suppressed while human serum albumin did not affect liposomal 9AC-G toxicity. This can be attributed to the liposomes protecting internal 9AC-G from interaction with human serum albumin, thereby preventing inactivation of 9AC-G. Stable retention and protection of 9AC-G within liposomes may allow high concentrations of active 9AC-G to reach tumors.

It was observed that the loading of parental 9AC and BQC resulted in an increased thickness of the liposome membrane (FIGS. 25 and 26). This suggests that the drugs accumulate in the lipid bilayer of liposomes by hydrophobic interactions. Decreased accumulation of drugs in the lipid bilayer of liposomes was achieved, by increasing drug accumulation in the aqueous core of liposomes by loading drugs in a glucuronide form. Core drug loading results in a more stable form of liposomal drugs compared to membrane loading. Also, drugs accumulating in the liposome membrane might cause defects in the membranes by destabilization of the bilayer structure as observed in FIG. 27.

Example 5: Parental Drug Regeneration

The glucuronidation of hydrophobic drugs leads to a decrease in the drug toxicity by enhanced water solubility and decreased cell membrane permeation. To fully take advantage of the glucuronidation of hydrophobic drugs for liposomal loading and retention, the parental compound should be regenerated after cellular uptake of the liposomes. As shown in FIG. 28, 9AC can be conjugated to a glucuronide residue which can interchange between a methylester form for loading and switched back to a glucuronide form for stable retention in liposomes. Addition of the lysosomal enzyme beta-glucuronidase to 9AC-G at pH 4.5 to mimic the lysosomal conditions efficiently regenerated 9AC, suggesting the potential of drug regeneration within lysosomes. To demonstrate the veracity of this suggested mechanism, cancer cell culture were incubated with liposomal 9AC-G or non-fluorescent fluorescein-di-G (FIG. 29) and the cells were periodically assayed for regeneration of the parental compounds (9AC and fluorescein). Cells have a natural capacity to uptake liposomes or nanoparticles by a mechanism known as pinocytosis. To increase the cellular uptake of the liposomes, a cell surface receptor was engineered by fusing the transmembrane domain of low density lipoprotein with the Fab fragment of an anti-PEG antibody. The anti-PEG portion of the artificial receptor can bind PEG on the surface of the liposomes and promote receptor-mediated endocytosis into the cells. In an in-vitro cell culture assay with HCC36 and MDA-MB468 human cancer cells, a time-dependent appearance of 9AC in the medium of the cells was observed after addition of 9AC-G liposomes. Without cells, the liposomal 9AC-G did not produce 9AC by itself, meaning that the cells were responsible for this regeneration (FIG. 32). When the liposome uptake by the cells was artificially increased by the engineered anti-PEG receptor, the amounts of 9AC found in the medium was also increased (FIG. 33). On the other hand, the amount of 9AC in the medium of cells was decreased when the cells were incubated at the same time with a beta-glucuronidase inhibitor or when the expression of beta-glucuronidase was decreased by treatment of the cells with RNAi. Altogether, the results show that the regeneration of the parental compounds requires uptake of the liposomes into cells and depends on the enzyme beta-glucuronidase. In addition, drug regeneration could be visualized in a confocal microscopy study with HCC36 cells that express anti-PEG receptors. Addition of liposomal fluorescein-di-G demonstrated the regeneration of fluorescein (green) within the cells, after colocolization of the liposomes (red) with lysosomes (magenta) (FIG. 34).

Example 6: Improved Pharmacokinetics

This example relates to a test of whether the liposomal formulation of 9AC-G could display prolonged pharmacokinetics when compared to free 9AC-G. Free and liposomal 9AC-G were delivered intravenously at 25 mg/kg to 12 to 16 weeks old female mice. The total serum concentrations of 9AC-G were monitored by collecting blood samples in which the plasma was isolated from the red blood cells by centrifugation. The serum proteins were precipitated in acetonitrile:methanol:0.2 M trichloroacetic acid (2:2:1, vol:vol mixture). Samples were centrifuged to eliminate precipitated proteins and diluted in buffer containing 1% triton X-100 to lyse the liposomes and analyze 9AC-G quantities by HPLC. FIG. 39 shows that the clearance of free 9AC-G was rapid (initial half-life=9.3 minutes; terminal half-life=38.6 minutes) compared to liposomal 9AC-G (initial half-life=36.5 minutes; terminal half-life=10.1 hours). At the same dosage, the plasma concentration of liposomal 9AC-G, 6 hours after injection, was found to be on average 350 folds higher than free 9AC-G. These results indicate that PEG-liposomes can be used as a glucuronide carrier to prolong the in-vivo half-life and are consistent with previous pharmacokinetics reports of liposomes[41-43].

Example 7: Anti-Cancer Activity of Liposomes

The anticancer activity of 9AC-G liposomes was assessed in-vitro and in-vivo. In-vitro, various human cancer cell lines (LS174T, HCT116, HT29, MDA-MB468, NCI-H2170, CL1-5, and SKMES-1) were seeded at 5000 cells per well in 96 well-plate overnight. Graded concentrations of 9ACG-liposomes or doxorubicin liposomes (Doxisome®) were added to the cells for 24 hours before removing the drug and incubating the cells for 72 additional hours. Cell proliferation was assayed by $^3$H-thymidine incorporation assay, where 1 µCi of $^3$H-thymidine diluted in culture medium were added to each well overnight. The cells were then harvested by trypsin on glass-fiber filters (PerkinElmer Unifilter®-96, GF/C®) and the radioactivity was measured on a TopCount scintillation counter (PerkinElmer). Final cell inhibition was determined as "% inhibition from control"= (c.p.m.(sample)×100)/c.p.m.(control)). Representative killing curves are shown in FIGS. 37 and 38, and $IC_{50}$ for the different cells and liposomal drugs are summarized in Table 1.

Next, in an in-vive model of breast cancer in NOD/SCID mice, $10^7$ MDA-MD468 cells were inoculated subcutaneously per mouse. The treatment was started when the tumors reached an average size of 75 to 100 mm$^3$. Mice were intravenously injected with 9AC-G liposomes at 10 mg/kg, free parental 9AC (2 mg/kg), or free 9AC-G (10 mg/kg). FIG. 40 shows monitoring of the weight of the mice during the treatment to evaluate the toxicity of this dosage. Appreciably, low toxicity was observed and the tumors were undetectable when treated with 9AC-G liposomes after 4 treatments for 6 over 7 mice, as shown in FIG. 41. In the other treatment groups, free 9AC or free 9AC-G had little effect on the tumor growth. The mice survival was significantly increased when the mice were treated with 9AC-G liposomes but not with free 9AC or free 9AC-G (FIG. 42). We observed that the amount of activated parental drug 9AC was over 30 folds higher in the tumor than in the blood 24 hours after injection of 9AC-G liposomes (FIG. 43). This phenomenon is likely due to the enhanced permeability and retention effect (EPR) by which nanoparticles accumulate and are retained in tumor through leaky blood tumor vasculature. Accumulation of 9AC-G liposomes in the tumor resulted in increased levels of 9AC being generated within the tumor itself.

By comparison, at day 84 after tumor inoculation, four weekly injections of liposomal doxorubicin (Doxisome® at 1 mg/kg) only reduced the tumor progression rate, while strong tumor suppression was achieved by 9AC-G liposomes (FIG. 44). Increasing the dose of Doxisome to 3 mg/kg, with the aim of improving antitumor activity, created major toxicity that was not observed with 9AC-G liposomes. As a result, all the mice died within 3 days after the third treatment with 3 mg/kg Doxisome (FIG. 45).

While embodiments have been shown and described, it will be apparent to those skilled in the art that many more modifications are possible without departing from the concepts herein. The claimed subject matter, therefore, is not to be restricted except in the spirit of the following claims.

TABLE 1

| Cells | Type | 9AC-G liposomes ($IC_{50}$ µM) | Doxisome ® ($IC_{50}$ µM) | Significance |
| --- | --- | --- | --- | --- |
| LS174T | Human colon adenocarcinoma | 0.18 ± 0.004 | 3.6 ± 0.07 | p < 0.0001 |
| HT29 | Human colorectal adenocarcinoma | 1.0 ± 0.02 | 6.9 ± 0.5 | p < 0.0001 |
| HCT116 | Human colorectal carcinoma | 0.85 ± 0.03 | 3.1 ± 0.09 | p < 0.0001 |
| CL1-5 | Human lung adenocarcinoma | 0.88 ± 0.1 | 3.4 ± 0.08 | p < 0.0001 |
| SKMES-1 | Human lung squamous cell carcinoma | 0.88 ± 0.3 | 1.13 ± 0.5 | N.S. |

TABLE 1-continued

| Cells | Type | 9AC-G liposomes (IC$_{50}$ µM) | Doxisome ® (IC$_{50}$ µM) | Significance |
|---|---|---|---|---|
| NCI-H2170 | Human lung squamous cell carcinoma | 1.2 ± 0.05 | 8.5 ± 2.2 | p < 0.01 |
| MDA-MD-468 | Human breast adenocarcinoma | 0.15 ± 0.03 | 2.4 ± 0.5 | P < 0.01 |

SUPPLEMENTARY TABLE 1

| Drugs | Year | Authors | References |
|---|---|---|---|
| 5-Fluorouracil | 1978 | Baba et al. | Ref. 16 |
| 9-Aminocamptothecin | 1999 | Leu et al. | Ref. 11 |
| Bleomycin | 2013 | Ediz et al. | Ref. 50 |
| Betulin | 2009 | Gauthier et al. | Ref. 18 |
| Cyclopamine | 2010 | Hamon et al. | Ref. 20 |
| CI-994 (Tacedinaline) | 2008 | Thomas et al. | Ref. 23 |
| Doxorubicin | 1996 | Houba et al. | Ref. 36 |
|  | 2001 | Houba et al. | Ref. 21 |
|  | 2012 | Grinda et al. | Ref. 34 |
|  | 2004 | De graaf et al. | Ref. 33 |
| Daunorubicin | 1997 | Bakina et al. | Ref. 30 |
| Etoposide | 2003 | Schmidt et al. | Ref. 14 |
| Monomethyl auristatin E (MMAE) | 2012 | Legigan et al. | Ref. 39 |
| p-hydroxyaniline mustard | 2004 | Wang et al. | Ref. 49 |
|  | 1999 | Cheng et al. | Ref. 17 |
|  | 1998 | Lougerstay-Madec et al. | Ref. 31 |
| PR-104A | 2011 | Gu et al. | Ref. 19 |
| Paclitaxel | 2006 | Alaoui et al. | Ref. 29 |
| Pyrrolo[2,1-c][1,4]benzodiazepine | 2008 | Kamal et al. | Ref. 37 |
| Quercetin | 2006 | Yang et al. | Ref. 25 |
| SN-38 (7-ethyl-10-hydroxycamptothecin) | 2003 | Angenault et al. | Ref. 32 |
| Suberoylanilide hydroxamic acid (SAHA) | 2007 | Thomas et al. | Ref. 47 |

REFERENCES

1. Bozzuto, G.; Molinari, A. Liposomes as Nanomedical Devices. *Int J Nanomedicine* 2015, 10, 975-999.
2. Pattni, B. S.; Chupin, V. V.; Torchilin, V. P. New Developments in Liposomal Drug Delivery. *Chem Rev* 2015, 115, 10938-10966.
3. Torchilin, V. P. Interview with Vladimir P Torchilin: Liposomal Carriers for Drug Delivery. *Ther Deliv* 2013, 4, 537-538.
4. Mallick, S.; Choi, J. S. Liposomes: Versatile and Biocompatible Nanovesicles for Efficient Biomolecules Delivery. *J Nanosci Nanotechnol* 2014, 14, 755-765.
5. Lasic, D. D.; Needham, D. The "Stealth" Liposome: A Prototypical Biomaterial. *Chem Rev* 1995, 95, 2601-2628.
6. Peer, D.; Karp, J. M.; Hong, S.; Farokhzad, O. C.; Margalit, R.; Langer, R. Nanocarriers as an Emerging Platform for Cancer Therapy. *Nat Nano* 2007, 2, 751-760.
7. Chen, H.; Kim, S.; Li, L.; Wang, S.; Park, K.; Cheng, J.-X. Release of Hydrophobic Molecules from Polymer Micelles into Cell Membranes Revealed by Förster Resonance Energy Transfer Imaging. *Proceedings of the National Academy of Sciences of the United States of America* 2008, 105, 6596-6601.
8. Zhigaltsev, I. V.; Maurer, N.; Akhong, Q.-F.; Leone, R.; Leng, E.; Wang, J.; Semple, S. C.; Cullis, P. R. Liposome-Encapsulated Vincristine, Vinblastine and Vinorelbine: A Comparative Study of Drug Loading and Retention. *Journal of Controlled Release* 2005, 104, 103-111.
9. Bhardwaj, U.; Burgess, D. J. Physicochemical Properties of Extruded and Non-Extruded Liposomes Containing the Hydrophobic Drug Dexamethasone. *International Journal of Pharmaceutics* 2010, 388, 181-189.
10. Bernsdorff, C.; Reszka, R.; Winter, R. Interaction of the Anticancer Agent Taxol (Paclitaxel) with Phospholipid Bilayers. *J Biomed Mater Res* 1999, 46, 141-149.
11. Leu, Y. L.; Roffler, S. R.; Chern, J. W. Design and Synthesis of Water-Soluble Glucuronide Derivatives of Camptothecin for Cancer Prodrug Monotherapy and Antibody-Directed Enzyme Prodrug Therapy (Adept). *J Med Chem* 1999, 42, 3623-3628.
12. Leu, Y. L.; Chen, C. S.; Wu, Y. J.; Chern, J. W. Benzyl Ether-Linked Glucuronide Derivative of 10-Hydroxycamptothecin Designed for Selective Camptothecin-Based Anticancer Therapy. *J Med Chem* 2008, 51, 1740-1746.
13. Prijovich, Z. M.; Leu, Y. L.; Roffler, S. R. Stability of the New Prodrug 9-Aminocamptothecin Glucuronide (9acg) in the Presence of Human Serum Albumin. *Biochem Pharmacol* 2003, 66, 1181-1187.
14. Schmidt, F.; Monneret, C. Prodrug Mono Therapy: Synthesis and Biological Evaluation of an Etoposide Glucuronide-Prodrug. *Bioorg Med Chem* 2003, 11, 2277-2283.
15. Rautio, J.; Kumpulainen, H.; Heimbach, T.; Oliyai, R.; Oh, D.; Jarvinen, T.; Savolainen, J. Prodrugs: Design and Clinical Applications. *Nat Rev Drug Discov* 2008, 7, 255-270.
16. Clerc, S.; Barenholz, Y. Liposome Drug-Loading Method and Composition. Google Patents: 1999.
17. Clerc, S.; Barenholz, Y. Loading of Amphipathic Weak Acids into Liposomes in Response to Transmembrane Calcium Acetate Gradients. *Biochim Biophys Acta* 1995, 1240, 257-265.

18. Alaoui, A. E.; Saha, N.; Schmidt, F.; Monneret, C.; Florent, J. C. New Taxol (Paclitaxel) Prodrugs Designed for Adept and Pmt Strategies in Cancer Chemotherapy. *Bioorg Med Chem* 2006, 14, 5012-5019.
19. Bakina, E.; Wu, Z.; Rosenblum, M.; Farquhar, D. Intensely Cytotoxic Anthracycline Prodrugs: Glucuronides. *J Med Chem* 1997, 40, 4013-4018.
20. Lougerstay-Madec, R.; Florent, J. C.; Monneret, C.; Nemati, F.; Poupon, M. F. Synthesis of Self-Immolative Glucuronide-Based Prodrugs of a Phenol Mustard. *Anticancer Drug Des* 1998, 13, 995-1007.
21. Angenault, S.; Thirot, S.; Schmidt, F.; Monneret, C.; Pfeiffer, B.; Renard, P. Cancer Chemotherapy: A Sn-38 (7-Ethyl-10-Hydroxycamptothecin) Glucuronide Prodrug for Treatment by a Pmt (Prodrug Monotherapy) Strategy. *Bioorg Med Chem Lett* 2003, 13, 947-950.
22. Baba, T.; Kidera, Y.; Kimura, N. T.; Aoki, K.; Kamura, T.; Taniguchi, S.; Nishikawa, K. 5-Fluorouracil O-Beta-D-Glucuronide as a Newly Synthesized Chemically Modified, Nontoxic Anticancer Drug. *Gan* 1978, 69, 283-284.
23. Gauthier, C.; Legault, J.; Lavoie, S.; Rondeau, S.; Tremblay, S.; Pichette, A. Synthesis and Cytotoxicity of Bidesmosidic Betulin and Betulinic Acid Saponins. *J Nat Prod* 2009, 72, 72-81.
24. de Graaf, M.; Pinedo, H. M.; Oosterhoff, D.; van der Meulen-Muileman, I. H.; Gerritsen, W. R.; Haisma, H. J.; Boven, E. Pronounced Antitumor Efficacy by Extracellular Activation of a Doxorubicin-Glucuronide Prodrug after Adenoviral Vector-Mediated Expression of a Human Antibody-Enzyme Fusion Protein. *Hum Gene Ther* 2004, 15, 229-238.
25. Grinda, M.; Clarhaut, J.; Renoux, B.; Tranoy-Opalinski, I.; Papot, S. A Self-Immolative Dendritic Glucuronide Prodrug of Doxorubicin. *Medchemcomm* 2012, 3, 68-70.
26. Grinda, M.; Clarhaut, J.; Tranoy-Opalinski, I.; Renoux, B.; Monvoisin, A.; Cronier, L.; Papot, S. A Heterodimeric Glucuronide Prodrug for Cancer Tritherapy: The Double Role of the Chemical Amplifier. *Chem Med Chem* 2011, 6, 2137-2141.
27. Hamon, F.; Renoux, B.; Chadeneau, C.; Muller, J. M.; Papot, S. Study of a Cyclopamine Glucuronide Prodrug for the Selective Chemotherapy of Glioblastoma. *Eur J Med Chem* 2010, 45, 1678-1682.
28. Houba, P. H.; Boven, E.; van der Meulen-Muileman, I. H.; Leenders, R. G.; Scheeren, J. W.; Pinedo, H. M.; Haisma, H. J. A Novel Doxorubicin-Glucuronide Prodrug Dox-Ga3 for Tumour-Selective Chemotherapy: Distribution and Efficacy in Experimental Human Ovarian Cancer. *Br J Cancer* 2001, 84, 550-557.
29. Houba, P. H.; Leenders, R. G.; Boven, E.; Scheeren, J. W.; Pinedo, H. M.; Haisma, H. J. Characterization of Novel Anthracycline Prodrugs Activated by Human Beta-Glucuronidase for Use in Antibody-Directed Enzyme Prodrug Therapy. *Biochem Pharmacol* 1996, 52, 455-463.
30. Kamal, A.; Tekumalla, V.; Raju, P.; Naidu, V. G.; Diwan, P. V.; Sistla, R. Pyrrolo[2,1-C][1,4]Benzodiazepine-Beta-Glucuronide Prodrugs with a Potential for Selective Therapy of Solid Tumors by Pmt and Adept Strategies. *Bioorg Med Chem Lett* 2008, 18, 3769-3773.
31. Leenders, R. G.; Damen, E. W.; Bijsterveld, E. J.; Scheeren, H. W.; Houba, P. H.; van der Meulen-Muileman, I. H.; Boven, E.; Haisma, H. J. Novel Anthracycline-Spacer-Beta-Glucuronide,-Beta-Glucoside, and -Beta-Galactoside Prodrugs for Application in Selective Chemotherapy. *Bioorg Med Chem* 1999, 7, 1597-1610.
32. Legigan, T.; Clarhaut, J.; Renoux, B.; Tranoy-Opalinski, I.; Monvoisin, A.; Berjeaud, J. M.; Guilhot, F.; Papot, S. Synthesis and Antitumor Efficacy of a Beta-Glucuronidase-Responsive Albumin-Binding Prodrug of Doxorubicin. *J Med Chem* 2012, 55, 4516-4520.
33. Prijovic, Z. M.; Leu, Y. L.; Roffler, S. R. Bqc-G, a Tumor-Selective Anti-Cancer Prodrug. Google Patents: 2013.
34. Prijovich, Z. M.; Chen, B. M.; Leu, Y. L.; Chern, J. W.; Roffler, S. R. Anti-Tumour Activity and Toxicity of the New Prodrug 9-Aminocamptothecin Glucuronide (9acg) in Mice. *Br J Cancer* 2002, 86, 1634-1638.
35. Prijovich, Z. M.; Leu, Y. L.; Roffler, S. R. Effect of Ph and Human Serum Albumin on the Cytotoxicity of a Glucuronide Prodrug of 9-Aminocamptothecin. *Cancer Chemother Pharmacol* 2007, 60, 7-17.
36. Nolen, H., 3rd; Fedorak, R. N.; Friend, D. R. Budesonide-Beta-D-Glucuronide: A Potential Prodrug for Treatment of Ulcerative Colitis. *J Pharm Sci* 1995, 84, 677-681.
37. Nolen, H. W., 3rd; Friend, D. R. Menthol-Beta-D-Glucuronide: A Potential Prodrug for Treatment of the Irritable Bowel Syndrome. *Pharm Res* 1994, 11, 1707-1711.
38. Renoux, B.; Legigan, T.; Bensalma, S.; Chadeneau, C.; Muller, J. M.; Papot, S. A New Cyclopamine Glucuronide Prodrug with Improved Kinetics of Drug Release. *Org Biomol Chem* 2011, 9, 8459-8464.
39. Skopp, G.; Lutz, R.; Potsch, L.; Ganssmann, B.; Klinder, K.; Schmidt, A.; Aderjan, R.; Mattern, R. An in Vitro Experiment for Postmortem Vascular Permeation. The Passage of Morphine and Morphine Glucuronides across a Vascular Wall. *J Forensic Sci* 1997, 42, 486-491.
40. Schmidt, L. E.; Rasmussen, A.; Norrelykke, M. R.; Poulsen, H. E.; Hansen, B. A. The Effect of Selective Bowel Decontamination on the Pharmacokinetics of Mycophenolate Mofetil in Liver Transplant Recipients. *Liver Transpl* 2001, 7, 739-742.
41. Thomas, M.; Clarhaut, J.; Tranoy-Opalinski, I.; Gesson, J. P.; Roche, J.; Papot, S. Synthesis and Biological Evaluation of Glucuronide Prodrugs of the Histone Deacetylase Inhibitor Ci-994 for Application in Selective Cancer Chemotherapy. *Bioorg Med Chem* 2008, 16, 8109-8116.
42. Thomas, M.; Rivault, F.; Tranoy-Opalinski, I.; Roche, J.; Gesson, J. P.; Papot, S. Synthesis and Biological Evaluation of the Suberoylanilide Hydroxamic Acid (Saha) Beta-Glucuronide and Beta-Galactoside for Application in Selective Prodrug Chemotherapy. *Bioorg Med Chem Lett* 2007, 17, 983-986.
43. Tietze, L. F.; Schuster, H. J.; Schmuck, K.; Schuberth, 1.; Alves, F. Duocarmycin-Based Prodrugs for Cancer Prodrug Monotherapy. *Bioorg Med Chem* 2008, 16, 6312-6318.
44. Wang, J.; Davis, M.; Li, F.; Azam, F.; Scatina, J.; Talaat, R. A Novel Approach for Predicting Acyl Glucuronide Reactivity Via Schiff Base Formation: Development of Rapidly Formed Peptide Adducts for Lc/Ms/Ms Measurements. *Chem Res Toxicol* 2004, 17, 1206-1216.
45. Cheng, T. L.; Chou, W. C.; Chen, B. M.; Chern, J. W.; Roffler, S. R. Characterization of an Antineoplastic Glucuronide Prodrug. *Biochem Pharmacol* 1999, 58, 325-328.
46. Gu, Y.; Tingle, M. D.; Wilson, W. R. Glucuronidation of Anticancer Prodrug Pr-104a: Species Differences, Identification of Human Udp-Glucuronosyltransferases, and Implications for Therapy. *J Pharmacol Exp Ther* 2011, 337, 692-702.

47. Yang, J. H.; Hsia, T. C.; Kuo, H. M.; Chao, P. D.; Chou, C. C.; Wei, Y. H.; Chung, J. G. Inhibition of Lung Cancer Cell Growth by Quercetin Glucuronides Via G2/M Arrest and Induction of Apoptosis. *Drug Metab Dispos* 2006, 34, 296-304.
48. Wang, S. M.; Chern, J. W.; Yeh, M. Y.; Ng, J. C.; Tung, E.; Roffler, S. R. Specific Activation of Glucuronide Prodrugs by Antibody-Targeted Enzyme Conjugates for Cancer Therapy. *Cancer Res* 1992, 52, 4484-4491.
49. Ediz, M.; Avcibasi, U.; Unak, P.; Muftuler, F. Z.; Medine, E. I.; Yurt Kilcar, A.; Demiroglu, H.; Gumuser, F. G.; Sakarya, S. Investigation of Therapeutic Efficiency of Bleomycin and Bleomycin-Glucuronide Labeled with (131)I on the Cancer Cell Lines. *Cancer Biother Radiopharm* 2013, 28, 310-319.
50. Rahman, A.; Carmichael, D.; Harris, M.; Roh, J. K. Comparative Pharmacokinetics of Free Doxorubicin and Doxorubicin Entrapped in Cardiolipin Liposomes. *Cancer Res* 1986, 46, 2295-2299.
51. Yates, T. J.; Lopez, L. E.; Lokeshwar, S. D.; Ortiz, N.; Kallifatidis, G.; Jordan, A.; Hoye, K.; Altman, N.; Lokeshwar, V. B. Dietary Supplement 4-Methylumbelliferone: An Effective Chemopreventive and Therapeutic Agent for Prostate Cancer. *J Natl Cancer Inst* 2015, 107.

The invention claimed is:

1. A method for loading a glucuronide alkylester of an anticancer drug into liposomes comprising:
   (a) preparing a liposome suspension with an external pH lower than 7 and an internal pH sufficiently high to convert the glucuronide alkylester to a glucuronide,
   (b) preparing the glucuronide alkylester by conjugating an alkylester group to the glucuronide, and
   (c) adding the glucuronide alkylester of an anticancer drug to the liposome suspension, wherein the glucuronide alkylester is loaded into the liposomes;
   wherein the glucuronide alkylester inside the liposomes is saponified to generate a glucuronide of an anticancer drug.

2. A method for loading a glucuronide methylester of an anticancer drug into liposomes comprising:
   (a) preparing a liposome suspension with an external pH lower than 7 and an internal pH sufficiently high to convert the glucuronide methylester to a glucuronide,
   (b) preparing the glucuronide methylester by conjugating a methylester group to the glucuronide, and
   (c) adding the glucuronide methylester of an anticancer drug to the liposome suspension, wherein the glucuronide methylester is loaded into the liposomes;
   wherein the glucuronide methylester inside the liposomes is saponified to generate a glucuronide of an anticancer drug.

3. The method of claim 1, wherein the method is effective to increase the liposomal retention of the glucuronide.

4. The method of claim 1, wherein the method is effective to load a glucuronidated hydrophilic form of a hydrophobic compound into the aqueous core of a liposome.

5. The method of claim 1, wherein the method is effective to load the glucuronide into the aqueous core of a liposome.

6. The method of claim 1, wherein the method is effective to improve the in-vivo half life of the glucuronide.

7. The method of claim 1, wherein the internal pH is from 7.5 to 8.5 and the external pH is from 4.5 to 5.5.

8. The method of claim 1, wherein the internal pH is about 8 and the external pH is about 5.

9. The method of claim 1, wherein the internal pH is 8 and the external pH is 5.

10. A method of loading a glucuronide of an anticancer drug into a liposome comprising
    (a) reacting a glucuronide in acidic methanol to form a glucuronide methylester (glucuronide-mE);
    (b) preparing a liposome, wherein the liposome has an internal pH from 7.5 to 8.5;
    (c) contacting the liposome with a solution comprising glucuronide-mE and having a pH from 4.5 to 5.5; and
    (d) purifying the liposome from the solution.

11. The method of claim 10, wherein the internal pH is about 8 and the external pH is about 5.

12. The method of claim 10, wherein the internal pH is 8 and the external pH is 5.

13. A method of preparing a liposome loaded with a glucuronide of an anticancer drug comprising
    (a) reacting a glucuronide in acidic methanol to form a glucuronide methylester (glucuronide-mE);
    (b) preparing a liposome, wherein the liposome has an internal pH from 7.5 to 8.5;
    (c) contacting the liposome with a solution comprising glucuronide-mE and having a pH from 4.5 to 5.5; and
    (d) purifying the liposome from the solution.

14. The method of claim 13, wherein the internal pH is about 8 and the external pH is about 5.

15. The method of claim 13, wherein the internal pH is 8 and the external pH is 5.

16. A liposome comprising a glucuronide of an anticancer drug, wherein the liposome is prepared by a process comprising adding a methylester of the glucuronide to a precursor liposome in a solution with an external pH, wherein the liposome has an internal pH that is greater than the external pH, and wherein the internal pH is sufficiently high to convert the methylester of the glucuronide to the glucuronide.

17. The liposome of claim 16, wherein the internal pH is greater than 7 and the external pH is less than 7.

18. The liposome of claim 16, wherein the internal pH is from 7.5 to 8.5 and the external pH is from 4.5 to 5.5.

19. The liposome of claim 16, wherein the internal pH is about 8 and the external pH is about 5.

20. The liposome of claim 16, wherein the internal pH is 8 and the external pH is 5.

21. A method of treating cancer or reducing size of a tumor comprising administering to a mammal or a human patient in need of treatment the liposome of claim 16 in an amount effective to reduce the size of the tumor;
    wherein the glucuronide of the anticancer drug after conversion inside the liposome has an octanol-water partition coefficient (Log P) of −1.5 to −2.5;
    wherein the cancer is a carcinoma; and
    wherein the anticancer drug is a camptothecin.

22. A method of treating cancer or reducing size of a tumor comprising administering to a mammal or a human patient in need of treatment the liposome prepared according to the method of claim 1 in an amount effective to reduce the size of the tumor;
    wherein the glucuronide after saponification has an octanol-water partition coefficient (Log P) of −1.5 to −2.5;
    wherein the cancer is a carcinoma; and
    wherein the anticancer drug is a camptothecin.

23. The method of claim 22, wherein the cancer is lung cancer, breast cancer or colon cancer and wherein the tumor origin is from lung, breast or colon.

24. The method of claim 22, wherein the anticancer drug is selected from the group consisting of 9-aminocamptothecin, and 5,6-dihydro-4H-benzo[de]quinoline-camptothecin.

* * * * *